United States Patent [19]
MacFarlane et al.

[11] Patent Number: 6,067,504
[45] Date of Patent: *May 23, 2000

[54] METHOD FOR CORRECTLY IDENTIFYING HAIR COLOR

[75] Inventors: Darby Simpson MacFarlane; David Kenneth MacFarlane, both of Hastings-on-Hudson; Fred W. Billmeyer, Jr., Schenectady, all of N.Y.

[73] Assignee: Chromatics Color Sciences International, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/476,809

[22] Filed: Jun. 8, 1995

Related U.S. Application Data

[63] Continuation-in-part of application No. 08/239,733, May 9, 1994, Pat. No. 5,671,735, which is a continuation-in-part of application No. 08/021,657, Feb. 22, 1993, Pat. No. 5,313,267, which is a continuation of application No. 07/204,938, Jun. 6, 1988, abandoned, and application No. 06/904,369, Sep. 8, 1986, abandoned, and a continuation-in-part of application No. 06/833,661, Feb. 21, 1986, abandoned, which is a continuation of application No. 06/514,618, Jul. 18, 1983, abandoned.

[51] Int. Cl.$^7$ ...................................................... A61B 5/00
[52] U.S. Cl. .......................... 702/1; 700/223; 356/402; 356/421; 356/422; 356/423; 356/425; 434/98; 434/102
[58] Field of Search ............................ 364/526; 356/402, 356/421, 422, 423, 425; 434/81, 98, 99, 100, 101, 102, 104, 377, 371, 94; 132/212; 702/1; 700/223; 358/518, 519; 382/165, 170

[56] References Cited

U.S. PATENT DOCUMENTS

| | | |
|---|---|---|
| 205,578 | 7/1878 | Rose et al. . |
| 1,582,122 | 4/1926 | Clapp . |
| 1,629,330 | 5/1927 | Adler . |
| 1,741,081 | 12/1929 | Stenz . |

(List continued on next page.)

FOREIGN PATENT DOCUMENTS

| | | |
|---|---|---|
| 655221 | 5/1995 | European Pat. Off. ........ A61B 5/103 |
| 1347400 | 11/1963 | France . |
| 1468339 | 12/1966 | France . |
| 2587181 | 3/1987 | France . |
| 1236984 | 3/1967 | Germany . |
| 3827457 | 6/1989 | Germany .......................... G01J 3/46 |
| 59020824 | 2/1984 | Japan . |
| 6037896 | 8/1985 | Japan ............................. G01N 33/49 |
| 0257328 | 12/1985 | Japan . |
| 8401665 | 12/1985 | Netherlands . |
| 2001595 | 10/1993 | Russian Federation ......... A61B 5/00 |

OTHER PUBLICATIONS

W.A. Gerrard, "The Measurement of Hair Colour", *International Journal of Cosmetic Science*, vol. 11, pp. 97–101 (1989).

*Patent Abstracts of Japan*, Sect. No. 276, vol. 8, No. 1131, p. 79 (May 26, 1984).

M. Kenny et al., "Transcutaneous Bilirubin Monitoring of Newborns", *Annals of the New York Academy of Sciences*, vol. 428, pp. 251–262 (1984).

R.E. Hannemann et al., "Neonatal Serum Bilirubin from Skin Reflectance", *Pediatric Research*, vol. 12, pp. 207–210 (1978).

(List continued on next page.)

*Primary Examiner*—Kamini Shah
*Attorney, Agent, or Firm*—Baker Botts L.L.P.

[57] ABSTRACT

Methods and apparatus for determining accurate hair color classificatinos and appropriate coloring agents to bring about a selected change of color include a table of hair color classifications, a color measuring instrument to arrive at Hunter L, a and b values for use in identifying a particular classification from the table and a database that identifies appropriate coloring agents based on a selection of coloring actions from a menu and the classifications of hair color.

17 Claims, 6 Drawing Sheets

U.S. PATENT DOCUMENTS

| | | |
|---|---|---|
| 1,979,119 | 10/1934 | Radzinsky . |
| 2,221,774 | 11/1940 | Bowser . |
| 3,003,388 | 10/1961 | Hunter et al. .............................. 35/17 |
| 3,533,399 | 10/1970 | Goldberg et al. . |
| 3,736,064 | 5/1973 | Kent et al. ............................. 356/195 |
| 4,029,085 | 6/1977 | Dewitt et al. .......................... 364/525 |
| 4,093,991 | 6/1978 | Christie, Jr. et al. .................. 364/525 |
| 4,135,497 | 1/1979 | Meyers et al. ......................... 128/214 |
| 4,241,738 | 12/1980 | Lübbers et al. ......................... 128/666 |
| 4,267,844 | 5/1981 | Yamanishi ............................. 128/633 |
| 4,302,971 | 12/1981 | Luk ......................................... 73/356 |
| 4,357,106 | 11/1982 | Tschirren et al. ....................... 356/44 |
| 4,423,736 | 1/1984 | Dewitt et al. .......................... 128/633 |
| 4,434,467 | 2/1984 | Scott ...................................... 364/400 |
| 4,479,499 | 10/1984 | Alfano et al. .......................... 128/665 |
| 4,561,850 | 12/1985 | Fabbri et al. .......................... 434/100 |
| 4,654,794 | 3/1987 | O'Brien ................................. 364/413 |
| 4,681,546 | 7/1987 | Hart ......................................... 434/99 |
| 4,723,554 | 2/1988 | Oman et al. ............................ 128/664 |
| 4,813,000 | 3/1989 | Wyman et al. ......................... 364/526 |
| 4,842,523 | 6/1989 | Bourdier et al. ....................... 434/371 |
| 4,857,071 | 8/1989 | Anderson ................................... 8/414 |
| 4,877,034 | 10/1989 | Atkins et al. ........................... 128/664 |
| 4,894,547 | 1/1990 | Leffell et al. ........................ 250/461.2 |
| 4,909,632 | 3/1990 | Macfarlane ............................ 356/402 |
| 4,964,874 | 10/1990 | Saphakkul .................................. 8/429 |
| 5,127,406 | 7/1992 | Yamaguchi ............................ 128/633 |
| 5,161,533 | 11/1992 | Cohen et al. ........................... 132/205 |
| 5,259,382 | 11/1993 | Kronberg ............................... 128/633 |
| 5,311,293 | 5/1994 | Macfarlane et al. ................... 356/421 |
| 5,313,267 | 5/1994 | Macfarlane et al. ................... 356/405 |
| 5,337,745 | 8/1994 | Benaron et al. ........................ 128/633 |
| 5,344,463 | 9/1994 | Chan et al. ................................ 8/408 |
| 5,353,790 | 10/1994 | Jacques et al. ......................... 128/633 |
| 5,387,977 | 2/1995 | Berg et al. .............................. 356/407 |
| 5,671,735 | 9/1997 | Macfarlane et al. ................... 128/633 |

OTHER PUBLICATIONS

F. Billmeyer, Jr., "Quantifying Color Appearance Visually and Instrumentally", *Color Research and Application*, vol. 13, pp. 140–145 (1988).

T. Hegyi, M.D., "Transcutaneous Bilirubinometry in the Newborn Infant: State of the Art", *Journal of Clinical Monitoring*, vol. 2, pp. 53–59 (1986).

R.E. Hanneman et al., "Evaluation of Minolta Bilirubin Meter as a Screening Device", *Pediatrics*, vol. 69, pp. 107–109 (1982).

D. Onks et al., "Effect of Melanin, Oxyhemoglobin and Bilirubin on Transcutaneous Bilirubinometry", *Acta. Pediatrica*, vol. 82, pp. 19–21 (1991).

F.D. Ortega et al., "Bilirrubinometria Transcutanea: Correlacion del Area de Medida Con La Espectropometria y Colorimetria Por Diazorreaccion", *Am. Exp. Pediarr.*, vol. 39, pp. 438–4–(1993).

R.E. Schumacher, "Noninvasive Measurement of Bilirubin in the Newborn", *Clinics in Perinatology*, vol. 17, pp. 417–435 (1990).

I. Yamanouchi et al., "Transcutaneous Bilirubinometry: Preliminary Studies of Noninvasive Transcutaneous Bilirubin Meters in the Okayama National Hospital", *Pediatrics*, vol. 65, pp. 195–202 (1980).

D. Tudehope et al., "Non–invasive Method of Measuring Bilirubin levels in Newborn Infants", *The Medical Journal of Australia*, vol. 1, pp. 165–168 (1982).

DIALOG World Patent Index database abstract of European Patent Application No. 655,221.

G. Wyszecki et al., *Color Science*, 2nd Edition (1982), Table of Contents, and pp.63–72.

F. Billmeyer & M. Saltzman, "Principles of Color Technology," 2nd ed., John Wiley & Sons, New York, NY 1981 pp. 18–19, 59–61, 92.

P.A. Lovett, Measurement of the Skin Color of Babies in Hospital, National Lighting Conference (1986).

C. Jackson, *Color Me Beautiful*, New York, Ballantine Books, Apr. 1981, pp. 25, 26, Color Palettes, 37–39, 41–59, 61–74, 143–147.

G. Pickney et al., *Your New Image Through Color & Line*, California Fashion Image/Crown Summit Books, Sep. 1981, pp. 1–3, 17, 21–29, 97–105, 111, 112, 120–127.

R. Evans, *An Introduction To Color*, Wiley, New York, 1948, pp. 26–27 and 87–90.

C.S. McCamy et al., A Color–Rendition Chart, J. Appl. Photogr. Eng. vol. 2, pp. 95–99 (1976).

C.A. Pearson, Face Colour As A Sign Of Tuberculosis, Color Res. Appl. vol. 7, pp. 31–33, (1982).

P.A. Lovett et al., Measurement of the Skin Color of Babies in Hospital, Proc. of CIBS Lighting Conference, 1986, HMSO, London, 1986, pp. 140–154.

Wyszecki et al., *Color Science*, 2nd Edition (1982), p. 63.

Advertisement for light meters sold by Minolta Corporation in Studio Photography, Nov. 1981, vol. 17, No. 11.

Advertisement for digital photometer by Photo Research in *Optical Spectra*, Nov., 1973.

DIALOG World Patent Index data base abstract for Netherlands Patent No. 8401665, published Dec. 16, 1985.

DIALOG World Patent Index database abstract for French Patent No. 2587181, published Mar. 20, 1987.

European Search Report for EPC Application No. 90302861.1, filed Mar. 16, 1990.

METHOD FOR CORRECTLY IDENTIFYING HAIR COLOR

This is a continuation-in-part of U.S. patent application Ser. No. 08/239,733, filed May 9, 1994, and now U.S. Pat. No. 5,671,735. No right of priority is claimed based upon any application filed earlier than May 9, 1994.

BACKGROUND OF THE INVENTION

This invention relates to a method and apparatus for the categorizing of hair color and hair color treatment agents for their interrelationship, and more particularly to a process and instrument for measuring three color characteristics of hair color and categorizing it and determining the effect of a wide variety of hair coloring agents thereon.

Hair coloring agent choices are often made by a consumer based on relatively vague indications of the color to be expected as a result of the use of the agent on an individual person's hair. This approach does not take into consideration the color of the hair that is to be treated and how interaction of that particular individual's hair color with the coloring agent will affect the resultant color.

No reliable source of information has been available to a private consumer regarding what the actual color of her or his hair is and what hair coloring agent will provide the hair color alteration that consumer seeks.

Consequently it can be seen there exists a need for procedures and apparatus that will accurately characterize an individual's hair color to enable selection of appropriate coloring agents for a desired color result. Likewise there exists a need for a reliable process and instrumentation to permit the use of the accurate color-characterization of an individual's hair color in the selection of hair coloring agents to effect hair color alterations of a type desired by the individual.

BRIEF SUMMARY OF THE INVENTION

According to this invention there is provided a method and apparatus for accurately characterizing the hair color of individuals to enable identification of the hair color and products suitable to achieve a desired change in hair color. More particularly, this invention relates to a method and apparatus for measuring color factors in an individual's hair color to assign that hair color to a classification previously determined to interact with identified hair coloring agents to bring about predictable color changes.

Through experimentation over a prolonged period, the applicants were able to compile a vast amount of information relating to coloration of virtually every imaginable hair color. Thousands of individual hair samples were treated with many various coloring agents. The hair color before and after such treatment was accurately, scientifically measured and characterized using known, reliable color measurement. Hair color was then assembled into a large number of categories based on ranges of the measured color factors. A database was assembled comprising the desired changes available through various hair coloring agents and the particular agents that would effect those changes in human hair to the various categories.

Instrumentation was implemented to measure from an individual's hair the color factors that operate to place the hair color in one of the numerous hair color classifications and to identify that classification to the individual or the individual's hair specialist. In addition, the instrumentation was arranged to allow for selection of a desired alteration in hair color, and on the basis of the gathered empirical data, hair coloring agents capable of effecting the desired change were located from within a database.

In an embodiment of the invention, the process for hair color analysis is carried out by measuring with a measuring instrument the value of a number of color factors in the color of an individual's hair at various sites, and then providing an indicator or table having a large number of hair color classifications defining ranges of those same color factors, and finally comparing the color factors of the indicator or table to the measured color factors to arrive at a classification of the individual's hair color.

In a preferred embodiment of the invention just described the color factors were Hunter L, a, b.

In an instrumentation implementing the process just described, a calorimeter was used to measure the color factors. The indicator or table having a large number of color classifications was retained in computer memory, and the comparison was made electronically between the memory-retained classifications and the measured color factors.

To use the process just described a list or menu of possible choices for varying hair color was presented. Upon selection that choice, along with the hair color classification previously determined, was used with a database of hair color classifications and associated product identifications empirically determined to effect the presented choices of color changes to locate in that database previously tested hair coloring agents capable of effecting the chosen action.

In one further embodiment of the process described, the color factors measured in an individual's hair color were Hunter L, a and b. Classifications of hair color provided in the indicator or table were percentages of grey in the hair of the individual. This embodiment enables the coloring of grey hair or partially grey hair to obtain an individual's natural hair coloring or another preferred hair color. This procedure required the selection of one of a number of categories of hair colors such as "light brown," "darkest blond," "light red," etc. The indicator or table that identified various hair color classifications was divided among broad hair color families or groups of categories and for an individual the particular hair family division of the indicator associated with that individual's broad family of hair color was found and then the ranges of color factors in that division were compared with the factors measured in the individual's hair to arrive at a classification.

In another embodiment of the invention, to arrive at a hair color treatment agent, a database of hair color treatment agents and classifications of color characteristics of individuals was compiled and an individual's color characteristics were determined by measurement of color factors, followed by comparison of those color factors with ranges contained in the database. In one embodiment the color characteristic of the individual that provided the basis for comparison was skin color.

DETAILED DESCRIPTION OF THE PREFERRED EMBODIMENT

Figure 1:
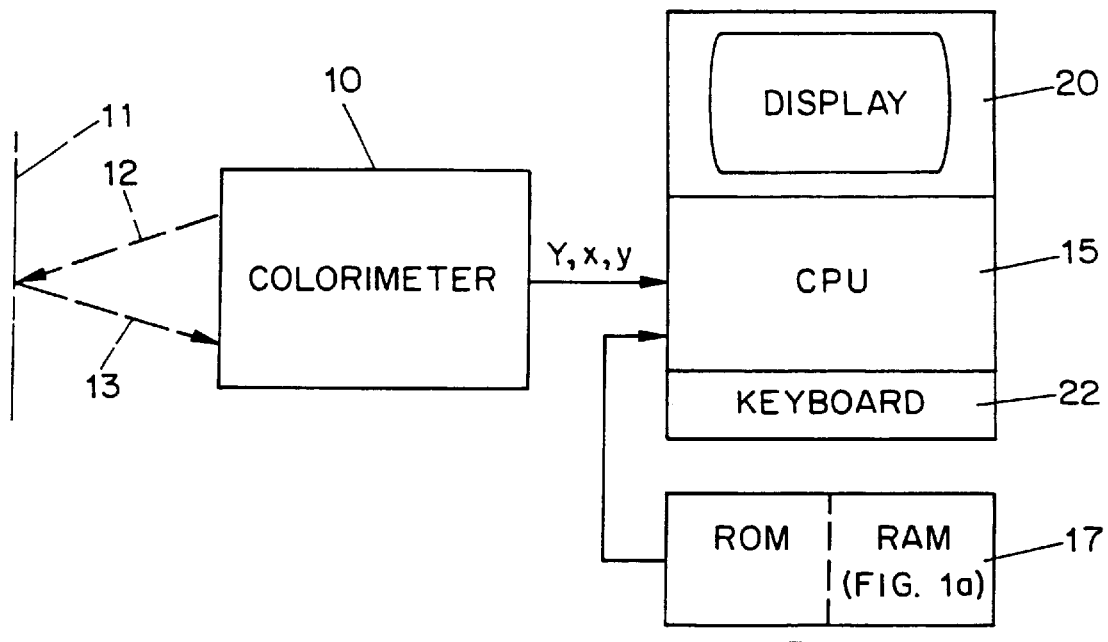
FIG. 1 is a block diagram illustration of an instrument for determining hair color Hunter L, a and b values and for comparing them with hair color classifications previously determined and stored in memory.

Any modern version of two general types of color-measuring instruments, calorimeters and spectrophotometers, is an example of instruments suitable for the hair color measurement according to a preferred embodiment of this invention. The basic components of either type of instrument are a light source, a sample illumination and viewing arrangement, a means of selecting certain wavelengths of light for the measurement, a detector of the light reflected from the sample, and some relatively simple computing capacity. In commercially available instruments the main purposes of the computing capacity are to store and apply calibration information and to calculate various color coordinates for later use. In FIG. 1, a color measuring instrument 10 is illustrated. An individual person's hair 11 is illuminated by the instrument as generally indicated by the broken line arrow 12, and the instrument receives illumination reflected from the hair 11 as generally indicated by the broken line arrow 13. Based on the illumination received by reflection from the hair, the instrument 10 develops the coordinates Y, x and y. In FIG. 1 the instrument 10 is a calorimeter, commercially available and suitable for development of the values Y, x and y.

Another type of instrument that can be used in the hair color categorization method according to this invention is the spectrophotometer that measures the hair reflectance at discrete wavelengths and from these data derives tristimulus values, from which can be computed the Hunter color values used to measure hair color for the purposes discussed below.

Important to the use of a commercial calorimeter of the kind employed for the color measurement instrument 10 of FIG. 1 is the calibration of the instrument using a standard. In the early use of an instrument of this kind by the inventors, the "Light Skin" sample from the Macbeth Color Checker, described in the publication of C. S. McCamy, H. Marcus, and J. G. Davidson, "A Color-Rendition Chart," J. Appl. Photogr. Eng. 2, 95–99 (1976) was used. A tile of this approximate color was selected for its greater durability as an instrument standard. It was found, however, that the use of the "Light Skin" painted paper as the primary standard did not adequately avoid the phenomenon known as metamerism, by which objects that look alike (have the same perceived color) under some kinds of light sources or to some observers do not match under other types of light sources or to other observers. By this phenomenon calorimeters may not read their colors the same as the average human observer would under the daylight type light source usually employed for visual observation, hence leading to an error in calorimeter calibration.

As an improved primary standard, the skin of a subject whose skin color measurements were highly reproducible and in the approximate center of the range of skin colors of the human population was selected. The spectral reflectance factors of the skin of this subject were carefully measured on a Macbeth 1500 Plus spectrophotometer (Macbeth, New Windsor, New York); these data are given in column 2 of Table I at the wavelengths listed in column 1. By using well-established techniques of computer color matching, carried out on an ACS 1800 system equipped with an ACS SpectroSensor II color measuring instrument (Datacolor International, Lawrenceville, N.J.) a colorant formulation matching this skin color was developed. The spectral reflectance factors for this match are given in column 3 of Table I. It may be seen that the data closely match those of column 2, indicating the absence of metamerism. Calculations according to the CIE 1976 CIELAB system showed that the two data sets match to within 0.27–0.36 units, less than can be perceived by human color vision, for daylight, incandescent light, and cool white fluorescent light, the three most commonly used light sources for the proposed applications.

The above-mentioned formulation was made up in a stable, durable material, and tiles were prepared as instrument standards. The spectral reflectance factors of one of these tiles are given in column 4 of Table I. It was found, however, that the improvement in calibration resulted in color coordinates that were significantly different from those obtained in the many studies made with the earlier system. A decision was made to adjust the calibration values of the new tiles in order to achieve consistent results between the new and old methods of calibration. Column 5 of Table I gives the adjusted set of spectral reflectance factors for the tile of column 4. The CIE and Hunter color coordinates, for measurement with the specular component excluded and calculated for CIE standard illuminant C and the 1931 2° CIE standard observer, are also tabulated for each of the samples in the table.

TABLE I

| Wavelengths, nm. | Skin Standard | Formulation | Tile, correct | Tile, adjusted |
|---|---|---|---|---|
| 400 | 19.03 | 20.70 | 21.51 | 16.67 |
| 420 | 18.96 | 20.69 | 21.10 | 16.93 |
| 440 | 21.53 | 21.68 | 20.99 | 17.65 |
| 460 | 25.36 | 24.43 | 23.27 | 20.56 |
| 480 | 28.06 | 28.30 | 27.82 | 25.67 |
| 500 | 30.13 | 30.77 | 29.03 | 27.94 |
| 520 | 31.19 | 31.31 | 29.38 | 28.24 |
| 540 | 30.01 | 30.84 | 28.48 | 27.59 |
| 560 | 31.41 | 30.76 | 28.22 | 27.33 |
| 580 | 32.85 | 34.01 | 31.49 | 30.12 |
| 600 | 44.37 | 43.54 | 42.58 | 40.52 |
| 620 | 51.24 | 51.57 | 51.27 | 47.93 |
| 640 | 54.56 | 55.09 | 55.56 | 51.10 |
| 660 | 57.09 | 57.60 | 59.22 | 53.82 |
| 680 | 58.67 | 60.41 | 61.82 | 56.55 |
| 700 | 59.95 | 62.69 | 63.93 | 58.87 |
| X | 37.14 | 37.28 | 36.14 | 33.76 |
| Y | 34.66 | 34.89 | 33.07 | 31.53 |
| Z | 28.50 | 28.54 | 27.63 | 24.20 |
| x | 0.3703 | 0.3702 | 0.3732 | 0.3732 |
| y | 0.3456 | 0.3464 | 0.3415 | 0.3523 |
| L | 58.87 | 59.07 | 57.51 | 56.15 |
| a | 9.31 | 9.02 | 11.54 | 9.05 |
| b | 12.51 | 12.70 | 11.77 | 13.75 |

With a suitable standard, basically, calibration is carried out by forcing the calorimeter 10 to give the desired color coordinates Y, x and y mentioned above, while utilizing the colorimeter with the standard tile chosen. The method of calibration is known for particular instruments and follows a series of steps prescribed by the manufacturer that need not be detailed here.

In hair color analysis, prior to each test of a subject the subject's hair should be free of dirt. The site should be well dried to avoid any wetness which may interfere with the reflection of light from the hair 11 to the instrument 10. In all cases with the instrument correctly calibrated, the instrument's measuring head or instrument orifice is placed against the site to be measured. Care is taken to avoid the admission of ambient light to the instrument. Pressing the instrument head firmly against the measurement site prevents the entry of ambient light. Additionally, it was determined that best results are obtained if one removes the instrument from the measurement site briefly, between illuminations. This can be provided for in software by a conventional delaying routine and, if desired, with an appropriate display instructing the user to remove the instrument briefly well away from the subject's hair.

In a calorimeter of the type shown in FIG. 1, at block 10 the instrument has an internal microprocessor or other computing capability so that it is able to develop the color coordinates Y, x and y from the measured values X, Y and Z (Y being the same in each case). Certain colorimeters develop the Hunter color coordinates L, a, and b. Since the degree of computation that the color measuring device 10 (i.e. colorimeter or spectrophotometer) internally performs varies, the manner of calculating the Hunter values from the tristimulus coordinates is useful to an understanding and practice of the invention and will enable correct use of a CPU by appropriate calculation to perform the invention with any commercially available calorimeter or spectrophotometer. Most modern color measuring instruments begin with measurement of the tristimulus values X, Y, and Z. From these can be derived the CIE chromaticity coordinates x and y:

$$x = X/(X+Y+Z) \tag{1}$$

$$y = Y/(X+Y+Z) \tag{2}$$

The instrument 10 of FIG. 1 outputs the triplet of values x, y and Y as the starting point for further calculations by a central processing unit which can be dedicated microprocessor circuitry or personal computer 15. The remaining two tristimulus values X and Z are available by computation as follows:

$$X = xY/y, \text{ and} \tag{3}$$

$$Z = (1-x-y)Y/y \tag{4}$$

In the preferred embodiment, in any event, the CPU according to FIG. 1 develops the Hunter values L, a and b. The Hunter L, a and b values are the three values derived by Richard S. Hunter in 1958. Richard S. Hunter, "Photoelectric Color Difference Meter," J. Opt. Soc. Am. 48, 985–995 (1958). The equations for these are:

$$L = 10 \, (Y)^{1/2} \tag{5}$$

$$a = 17.5 \, (1.02 \, X - Y)/Y^{1/2} \tag{6}$$

$$b = 7.0 \, (Y - 0.847 \, Z)/Y^{1/2} \tag{7}$$

where L is a lightness coordinate whose values correlate better with the visual perceptions of the lightness of object colors than do values of Y; a is a coordinate denoting redness or greenness, for which positive values denote that the color is red rather than its opponent color green, and negative values of a denote the opposite; and b is a yellowness-blueness coordinate, for which positive values denote that the color is yellow rather than the opponent color blue, and negative values of b denote the opposite. For yellow colors, starting with a=b=0 and an appropriate high value of L, which would be a light grey, increasing positive values of b result in a series of colors that may be described as light yellowish grey, pale yellow, light yellow, brilliant yellow and vivid yellow, in turn. Thus b is a measure of the "intensity" of the yellow color.

In the particular arrangement of FIG. 1, wherein the colorimeter 10 produces the values Y, x, y, the computer 15 derives the Hunter values L, a and b.

Figure 2:
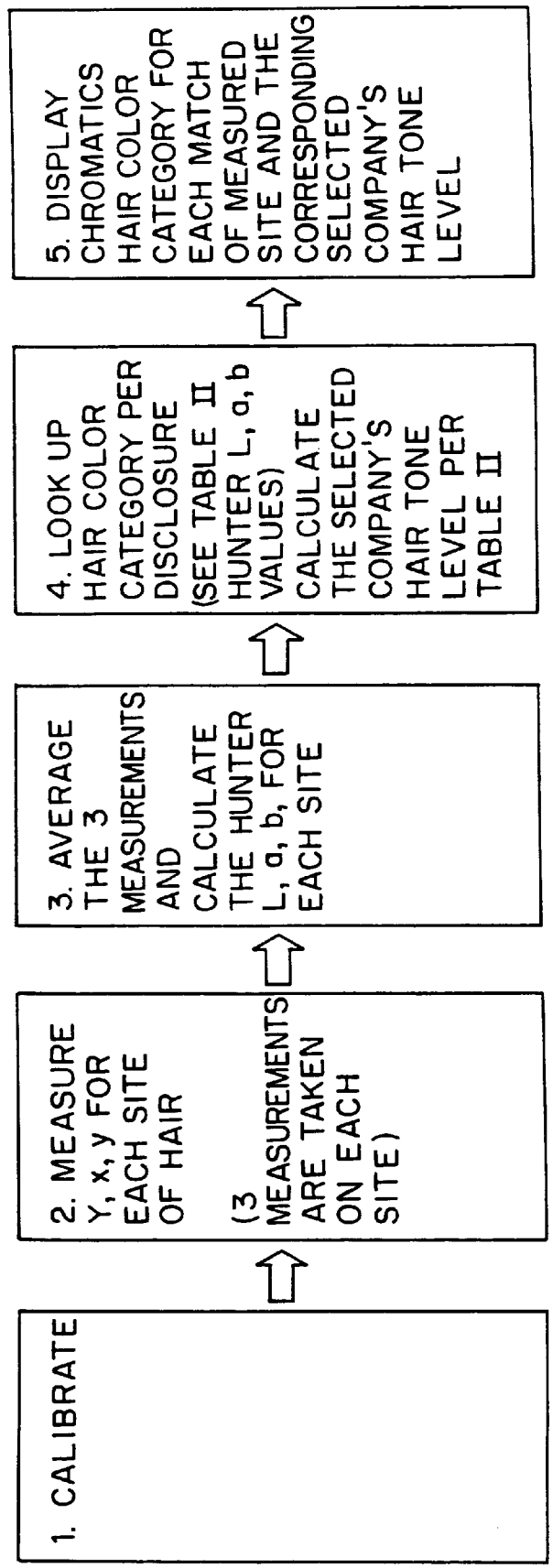
FIG. 2 is a schematic illustration in block diagram form illustrating the steps in the process of arriving at hair color classification of an individual.

Following the procedure represented in FIG. 2, the colorimeter is calibrated as described above in step 1. In step 2, the values of Y, x and y are measured for each of multiple sites on the subject's hair. Preferably the top, each side, the back of the subject's head, the color of the hair at the roots and at its ends, are measured. Three measurements are taken at each site. In step 3, the measurements are averaged to arrive at an Y, x and y for each site and, from the average for each site, Hunter L, a and b for each site is calculated.

In step 4 of FIG. 2, the values of Hunter L, a and b are compared to the values of Hunter L, a and b of the color categories 1, 2, 3, 4, 5, 6 etc. of the Hair Categories table of Table II set forth below. This, then, identifies the category of the subject's hair coloring at each of the measured sites. Each Hair Category in Table II, set forth below, has in association with it the hair color name, such as Black-Cool, Darkest Dark Brown-Cool, etc., an identification of one or more manufacturer's "Levels" which are commonly indicated upon a manufacturer's product to indicate products recommended for individuals with particular hair color. In other words, the identification of hair category or classification can also indicate to the subject or the subject's hair specialist the designation or level that the subject should seek out in a particular manufacturer's line of products.

TABLE II

| | | HAIR CATEGORIES | | | | | | | Clairol | | L'Oreal | |
| | | | L | | a | | b | | | | | |
| | CATEGORY NAME | Min | Max | Min | Max | Min | Max | Level | Pigmt | Level | Pigmt |
|---|---|---|---|---|---|---|---|---|---|---|---|---|
| 1. A | Black Cool | 0.00 | 14.00 | 10.00 | 3.00 | 10.00 | 5.00 | 1 | Red Brown | M1 | None |
| 2. B | Darkest Dark Brown Cool | 14.00 | 16.00 | 10.00 | 3.00 | 10.00 | 1.00 | 2 | Red Brown | M3 | None |
| 3. B | Darkest Dark Brown Border C/W - C | 14.00 | 16.00 | 10.00 | 3.00 | 1.00 | 1.15 | 2 | Red Brown | M3 | None |

TABLE II-continued

|  |  |  | \multicolumn{6}{c}{HAIR CATEGORIES} | \multicolumn{2}{c}{Clairol} | \multicolumn{2}{c}{L'Oreal} |
| | | | L | | a | | b | | | | | |
| | | CATEGORY NAME | Min | Max | Min | Max | Min | Max | Level | Pigmt | Level | Pigmt |
|---|---|---|---|---|---|---|---|---|---|---|---|---|
| 4. | B | Darkest Dark Brown Border C/W - W | 14.00 | 16.00 | 10.00 | 3.00 | 1.15 | 1.25 | 2 | Red Brown | M3 | None |
| 5. | B | Darkest Dark Brown Warm | 14.00 | 16.00 | 10.00 | 3.00 | 1.25 | 3.00 | 2 | Red Brown | M3 | None |
| 6. | C | Darker Dark Brown - Cool | 16.00 | 19.00 | 10.00 | 3.00 | −10.00 | 2.70 | 3 | Red Orange | M4 | Red |
| 7. | C | Darker Dark Brown - Border C/W - C | 16.00 | 19.00 | 10.00 | 3.00 | 2.70 | 2.95 | 3 | Red Orange | M4 | Red |
| 8. | C | Darker Dark Brown - Border C/W - W | 16.00 | 19.00 | −10.00 | 3.00 | 2.95 | 3.20 | 3 | Red Orange | M4 | Red |
| 9. | C | Darker Dark Brown - Warm | 16.00 | 19.00 | −10.00 | 3.00 | 3.20 | 10.00 | 3 | Red Orange | M4 | Red |
|  |  | FLAG: Darker Dark Brown (Auburn Tones) Cool | 16.00 | 19.00 | 2.00 | 3.00 | 10.00 | 2.70 | 3 | Red Orange | M4 | Red |
|  |  | Darker Dark Brown (Auburn Tones) Warm | 16.00 | 19.00 | 2.00 | 3.00 | 3.20 | 10.00 | 3 | Red Orange | M4 | Red |
| 10. | D | Brown - Cool | 19.00 | 22.00 | 0.00 | 6.00 | 10.00 | 2.95 | 4 | Red Orange | M5 | Red Orange |
| 11. | D | Brown - Border C/W - C | 19.00 | 22.00 | 0.00 | 6.00 | 2.95 | 3.20 | 4 | Red Orange | M5 | Red Orange |
| 12. | D | Brown - Border C/W - W | 19.00 | 22.00 | 0.00 | 6.00 | 3.20 | 3.45 | 4 | Red Orange | M5 | Red Orange |
| 13. | D | Brown - Warm | 19.00 | 22.00 | 0.00 | 6.00 | 3.45 | 10.00 | 4 | Red Orange | M5 | Red Orange |
|  |  | FLAG: Brown (Auburn Tones) - Warm | 19.00 | 22.00 | 3.50 | 6.00 | 3.45 | 10.00 | 4 | Red Orange | M5 | Red Orange |
|  |  | Brown (Auburn Tones) - Cool | 19.00 | 22.00 | 3.50 | 6.00 | 10.00 | 3.45 | 4 | Red Orange | M5 | Red Orange |
| 14. | E | Medium Brown - Cool | 22.00 | 27.00 | 1.00 | 6.00 | −10.00 | 3.75 | 5 | Orange | M6 | Orange |
| 15. | E | Medium Brown - Border C/W - C | 22.00 | 27.00 | 1.00 | 6.00 | 3.75 | 4.00 | 5 | Orange | M6 | Orange |
| 16. | E | Golden Med Brown - Border C/W - W | 22.00 | 27.00 | 1.00 | 6.00 | 4.00 | 4.25 | 5 | Orange | M6 | Orange |
| 17. | E | Golden Medium Brown - Warm | 22.00 | 27.00 | 1.00 | 6.00 | 4.25 | 10.00 | 5 | Orange | M6 | Orange |
|  |  | FLAG: Med Brown (Auburn Tones) Warm | 22.00 | 27.00 | 3.50 | 6.00 | 4.25 | 10.00 | 5 | Orange | M6 | Orange |
|  |  | Med Brown (Auburn Tones) Cool | 22.00 | 27.00 | 3.50 | 6.00 | 10.00 | 4.25 | 5 | Orange | M6 | Orange |
| 18. | F | Darkest Medium Blonde - Cool | 27.00 | 28.00 | 1.80 | 6.00 | 5.00 | 6.00 | 6 | Gold Orange | M7 | Yellow Orange |
| 19. | F | Darkest Med Blonde Border C/W - C | 27.00 | 28.00 | 1.80 | 5.00 | 6.00 | 6.50 | 6 | Gold Orange | M7 | Yellow Orange |
| 20. | F | Darkest Med Blonde Border C/W - W | 27.00 | 28.00 | 5.00 | 6.00 | 6.00 | 6.50 | 6 | Gold Orange | M7 | Yellow Orange |
| 23. | F | Darkest Medium Blonde - Warm | 27.00 | 28.00 | 1.80 | 6.00 | 6.50 | 15.00 | 6 | Gold Orange | M7 | Yellow Orange |
| 22. | G | Medium Blonde - Cool | 28.00 | 31.00 | 1.80 | 6.00 | −5.00 | 6.00 | 6 | Gold Orange | M8 | Yellow |
| 23. | G | Medium Blonde - Border C/W - C | 28.00 | 31.00 | 1.80 | 5.00 | 6.00 | 6.50 | 6 | Gold Orange | M8 | Yellow |
| 24. | G | Med Golden Blonde - Border C/W - W | 28.00 | 31.00 | 5.00 | 6.00 | 6.00 | 6.50 | 6 | Gold Orange | M8 | Yellow |
| 25. | G | Medium Golden Blonde - Warm | 28.00 | 31.00 | 1.80 | 6.00 | 6.50 | 15.00 | 6 | Gold Orange | M8 | Yellow |
| 26. | H | Lightest Med Blonde - Cool | 31.00 | 33.00 | 1.80 | 6.00 | −5.00 | 6.00 | 7 | Gold | M8 | Yellow |
| 27. | H | Ltst Med Blonde - Border C/W - C | 31.00 | 33.00 | 1.80 | 5.00 | 6.00 | 6.50 | 7 | Gold | M8 | Yellow |
| 28. | H | Ltst Med Blonde - Border C/W - W | 31.00 | 33.00 | 5.00 | 6.00 | 6.00 | 6.50 | 7 | Gold | M8 | Yellow |
| 29. | H | Lightest Med Blonde Warm | 31.00 | 33.00 | 1.80 | 6.00 | 6.50 | 15.00 | 7 | Gold | M8 | Yellow |
| 30. | I | Light Blonde Cool | 33.00 | 16.00 | 1.80 | 6.00 | 5.00 | 7.00 | 7 | Gold | M9 | Pale Yellow |
| 31. | I | Light Blonde - Border C/W - C | 33.00 | 16.00 | 1.80 | 5.00 | 7.00 | 7.50 | 7 | Gold | M9 | Pale Yellow |

TABLE II-continued

| | | CATEGORY NAME | HAIR CATEGORIES | | | | | | Clairol | | L'Oreal | |
|---|---|---|---|---|---|---|---|---|---|---|---|---|
| | | | L | | a | | b | | | | | |
| | | | Min | Max | Min | Max | Min | Max | Level | Pigmt | Level | Pigmt |
| 32. | I | Light Blonde - Border C/W - W | 33.00 | 16.00 | 5.00 | 6.00 | 7.00 | 7.50 | 7 | Gold | M9 | Pale Yellow |
| 33. | I | Light Blonde - Warm | 33.00 | 36.00 | 1.80 | 6.00 | 7.50 | 20.00 | 7 | Gold | M9 | Pale Yellow |
| 34. | J | Lighter Blonde - Cool | 36.00 | 40.00 | 1.80 | 6.00 | −5.00 | 8.00 | 8 | Deep Yellow | M9 | Pale Yellow |
| 35. | J | Lighter Blonde - Border C/W - C | 36.00 | 40.00 | 1.80 | 5.00 | 8.00 | 8.50 | 8 | Deep Yellow | M9 | Pale Yellow |
| 36. | J | Lighter Blonde - Border C/W - W | 36.00 | 40.00 | 5.00 | 6.00 | 8.00 | 8.50 | 8 | Deep Yellow | M9 | Pale Yellow |
| 37. | J | Lighter Blonde - Warm | 36.00 | 40.00 | 1.80 | 6.00 | 8.50 | 20.00 | 8 | Deep Yellow | M9 | Pale Yellow |
| 38. | F | Lightest Blonde - Cool | 40.00 | 50.00 | 1.80 | 7.00 | −5.00 | 9.00 | 9 | Pale Yellow | M10 | Pale Yellow |
| 39. | K | Lightest Blonde - Border C/W - C | 40.00 | 50.00 | 1.80 | 5.00 | 9.00 | 10.00 | 9 | Pale Yellow | M10 | Pale Yellow |
| 40. | K | Lightest Blonde - Border C/W - W | 40.00 | 50.00 | 5.00 | 7.00 | 9.00 | 10.00 | 9 | Pale Yellow | M10 | Pale Yellow |
| 41. | K | Lightest Blonde - Warm | 40.00 | 50.00 | 1.80 | 7.00 | 10.00 | 30.00 | 9 | Pale Yellow | M10 | Pale Yellow |
| 42. | L | Lightest Blonde - Cool | 50.00 | 80.00 | 1.80 | 7.00 | −5.00 | 9.00 | 10 | Pale Yellow | M10 | Pale Yellow |
| 43. | L | Lightest Blonde - Border C/W - C | 50.00 | 80.00 | 1.80 | 5.00 | 9.00 | 10.00 | 10 | Pale Yellow | M10 | Pale Yellow |
| 44. | L | Lightest Blonde - Border C/W - W | 50.00 | 80.00 | 5.00 | 7.00 | 9.00 | 10.00 | 10 | Pale Yellow | M10 | Pale Yellow |
| 45. | L | Lightest Blonde - Warm | 50.00 | 80.00 | 1.80 | 7.00 | 10.00 | 30.00 | 10 | Pale Yellow | M10 | Pale Yellow |
| 46. | M | Light Red - Cool | 22.00 | 28.00 | 6.00 | 30.00 | −5.00 | 3.50 | 5 (with Red Violet, Neutral or Blue Violet tones) | Orange | M6 (with Ash, Iridescent or Auburn tones) | Orange |
| 47. | M | Light Red - Border C/W - C | 22.00 | 28.00 | 6.00 | 30.00 | 3.50 | 3.75 | 5 (with Red Violet, Neutral or Blue Violet tones) | Orange | M6 (with Ash, Iridescent or Auburn tones) | Orange |
| 48. | M | Light Red - Border C/W - W | 22.00 | 28.00 | 6.00 | 30.00 | 3.75 | 4.00 | 5 (with Red, Gold or Red Orange tones) | Orange | M6 (with Gold or Copper tones) | Orange |
| 49. | M | Light Red - Warm | 22.00 | 28.00 | 6.00 | 30.00 | 4.00 | 30.00 | 5 (with Red, Gold or Red Orange tones) | Orange | M6 (with Gold or Copper tones) | Orange |
| 50. | N | Medium Red - Cool | 19.00 | 22.00 | 6.00 | 30.00 | 10.00 | 3.50 | 4 (with Red Violet, Neutral or Blue Violet tones) | Red Orange | M5 (with Ash, Iridescent or Auburn tones) | Red Orange |
| 51. | N | Medium Red Border C/W - C | 19.00 | 22.00 | 6.00 | 30.00 | 3.50 | 3.75 | 4 (with Red Violet, Neutral or Blue Violet tones) | Red Orange | M5 (with Ash, Iridescent or Auburn tones) | Red Orange |
| 52. | N | Medium Golden Red - Border C/W - W | 19.00 | 22.00 | 6.00 | 30.00 | 3.75 | 4.00 | 4 (with Red Gold or Red Orange tones) | Red Orange | M5 (with Gold or Copper tones) | Red Orange |
| 53. | N | Medium Golden Red - Warm | 19.00 | 22.00 | 6.00 | 30.00 | 4.00 | 30.00 | 4 (with Red, Gold or Red Orange tones) | Red Orange | M5 (with Gold or Copper tones) | Red Orange |
| 54. | O | Dark Red - Cool | 14.00 | 19.00 | 3.00 | 30.00 | −10.00 | 2.50 | 2/3 (with Red Violet, Neutral or Blue Violet tones) | Red Orange | M4 (with Ash, Iridescent or Auburn tones) | Red Orange |
| 55. | O | Dark Red - Border C/W - C | 14.00 | 19.00 | 3.00 | 30.00 | 2.50 | 2.75 | 2/3 (with Red Violet, Neutral or Blue Violet tones) | Red Orange | M4 (with Ash, Iridescent or Auburn tones) | Red Orange |
| 56. | O | Dark Red - Border C/W - W | 14.00 | 19.00 | 3.00 | 30.00 | 2.75 | 3.00 | 2/3 (with Red, Gold or Red Orange tones) | Red Orange | M4 (with Gold or Copper tones) | Red Orange |

TABLE II-continued

| | | HAIR CATEGORIES | | | | | | Clairol | | L'Oreal | |
|---|---|---|---|---|---|---|---|---|---|---|---|
| | | L | | a | | b | | | | | |
| | CATEGORY NAME | Min | Max | Min | Max | Min | Max | Level | Pigmt | Level | Pigmt |
| 57. O | Dark Red Warm | 14.00 | 19.00 | 3.00 | 30.00 | 3.00 | 30.00 | 2/3 (with Red, Gold or Red Orange tones) | Red Orange | M4 (with Gold or Copper tones) | Red Orange |
| 58. P | Red Blonde | 27.00 | 40.00 | 6.00 | 30.00 | 6.00 | 30.00 | 6/7/8 (with Red, Gold or Red Orange tones) | Yellow | M7/M8 (with Gold or Copper tones) | Yellow |
| 59. Q | Red Blonde | 40.00 | 50.00 | 7.00 | 30.00 | 6.00 | 30.00 | 9/10 (with Red, Gold or Red Orange tones) | Pale Yellow | M9 (with Gold or Copper tones) | Pale Yellow |
| 60. R | Red Blonde | 50.00 | 80.00 | 7.00 | 30.00 | 6.00 | 30.00 | 9/10 (with Red, Gold or Red Orange tones) | Pale Yellow | M9 (with Gold or Copper tones) | Pale Yellow |
| 61. S | Black/Dk Brown/Med Brown/Brown w/70%–90% Grey - Cool | 27.00 | 50.00 | 10.00 | 1.80 | –10.00 | 3.75 | | | | |
| 62. S | Black/Dk Brown/Med Brown/Brown w/70–90% Grey - Border C/W - C | 27.00 | 50.00 | –10.00 | 1.80 | 3.75 | 4.00 | | | | |
| 63. S | Black/Dk Brown/Med Brown/Brown w/70–90% Grey - Border C/W - W | 27.00 | 50.00 | –10.00 | 1.80 | 4.00 | 4.25 | | | | |
| 64. S | Black/Dk Brown/Med Brown/Brown w/70%–90% Grey - Warm | 27.00 | 50.00 | –10.00 | 1.80 | 4.25 | 10.00 | | | | |

The Hair Categories Table II may further identify for the subject or his or her specialist the pigment designation given the manufacturers to the particular color. In step 5, the color category for each match of measured site and the corresponding selected company's hair tone level is displayed.

The hair color categories for the several measured sites, then, can be used by the subject or her or his hair specialist to allow for accurate assessment of the hair color to be dyed and to choose a product for hair coloring. As will be appreciated, the category or classification may vary from site to site and this will inform the subject or specialist whether it will be necessary to use varying products or longer or shorter periods of application at varying sites to achieve a hair coloration desired. In other words, dark roots might be treated differently than light ends.

Figure 3:
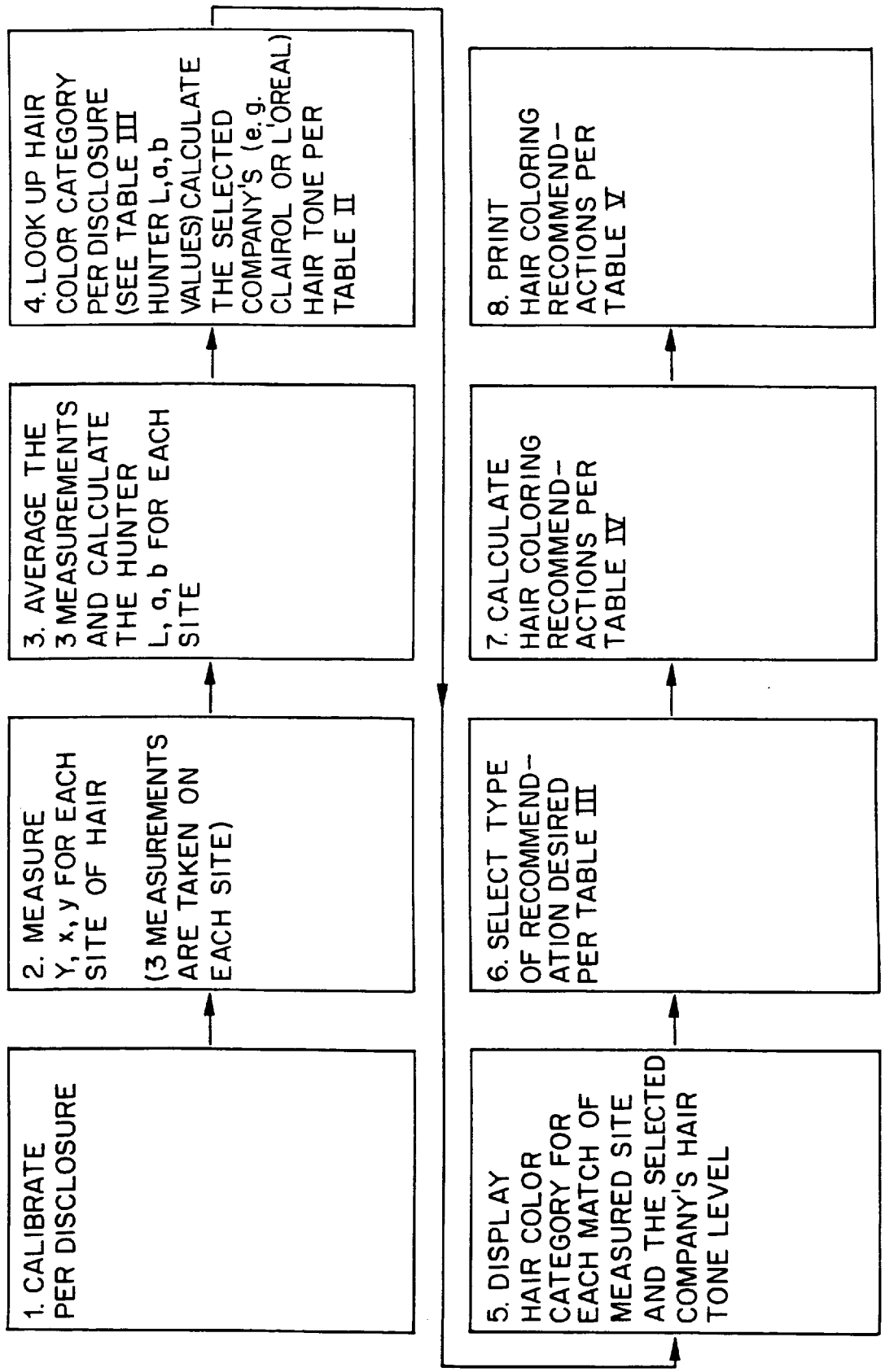
FIG. 3 is a schematic illustration in block diagram form illustrating the steps in the process of using hair color classification and a database to arrive at a coloring agent for making a selected alteration in hair color.

In accordance with the further method according to FIG. 3 #steps 1 through 5, a hair coloring agent recommendation is made to achieve a subject's desired coloration change. Such steps are the same as steps 1 through 5 of FIG. 2, discussed above. Once having determined the correct color categories for each measured site, a menu of possible actions (Table III, set forth below) affecting hair color is displayed and one such action is chosen by the subject or hair specialist.

TABLE III

MENU OF HAIR COLOR OPTIONS

1. Match Natural Hair Color
2. Make Natural Hair Color Warmer
3. Make Natural Hair Color Cooler
4. Highlight Natural Hair Color
5. Make Natural Hair Color Slightly Darker
6. Make Natural Hair Color Slightly Lighter TABLE III-continued

MENU OF HAIR COLOR OPTIONS

7. Make Natural Hair Color Darker
8. Make Natural Hair Color Lighter
9. Make Natural Hair Color Warmer and Slightly Darker
10. Make Natural Hair Color Warmer and Slightly Lighter
11. Make Natural Hair Color Warmer and Darker
12. Make Natural Hair Color Warmer and Lighter
13. Make Natural Hair Color Cooler and Slightly Darker
14. Make Natural Hair Color Cooler and Slightly Lighter
15. Make Natural Hair Color Cooler and Darker
16. Make Natural Hair Color Cooler and Lighter
17. Make Natural Hair Color Warmer with Highlights
18. Make Natural Hair Color Cooler with Highlights
19. Make Tinted Hair Color Warmer
20. Make Tinted Hair Color Cooler
21. Highlight Tinted Hair Color
22. Make Tinted Hair Color Slightly Darker
23. Make Tinted Hair Color Slightly Lighter
24. Make Tinted Hair Color Darker
25. Make Tinted Hair Color Lighter
26. Make Tinted Hair Color Warmer and Slightly Darker
27. Make Tinted Hair Color Warmer and Slightly Lighter
28. Make Tinted Hair Color Warmer and Darker
29. Make Tinted Hair Color Warmer and Lighter
30. Make Tinted Hair Color Cooler and Slightly Darker
31. Make Tinted Hair Color Cooler and Slightly Lighter
32. Make Tinted Hair Color Cooler and Darker
33. Make Tinted Hair Color Cooler and Lighter
34. Make Tinted Hair Color Warmer with Highlights
35. Make Tinted Hair Color Cooler with Highlights Using that selection and the hair color category, a database (Table IV, set forth below) is consulted as indicated at step 6 and at step 7 products are identified from Table V, set forth below, of a given manufacturer that will accomplish the sought-after result.

TABLE IV

| | Category Name | DATABASE LMin | LMax | aMin | aMax | bMin | bMax | CW | Level |
|---|---|---|---|---|---|---|---|---|---|
| 1 | A. BLACK-COOL | 0.00 | 14.00 | −10.00 | 3.00 | −10.00 | 5.00 | 1 | 1 |
| | Clairol: #1 | | | | | | | −1:01 −2:01 +1:02 +2:02 Pig: 1 File: 011 | |
| | L'Oreal: M1 | | | | | | | −1:01 −2:01 +1:02 +2:02 Pig: 0 File: 011 | |
| 2 | B. DARKEST DARK BROWN-COOL | 34.00 | 16.00 | −10.00 | 3.00 | −10.00 | 1.00 | 1 | 2 |
| | Clairol: #2 | | | | | | | −1:01 −2:01 +1:03 +2:03 Pig: 1 File: 021 | |
| | L'Oreal: M3 | | | | | | | −1:01 −2:01 +1:03 +2:03 Pig: 0 File: 021 | |
| 3 | B. DARKEST DARK BROWN-BORDER C/W--COOL | 14.00 | 16.00 | −10.00 | 3.00 | 1.00 | 1.15 | 2 | 2 |
| | Clairol: #2 | | | | | | | −1:01 −2:01 +1:03 +2:03 Pig: 1 File: 021 | |
| | L'Oreal: M3 | | | | | | | −1:01 −2:01 +1:03 +2:03 Pig: 0 File: 021 | |
| 4 | B. DARKEST DARK BROWN-BORDER C/W--WARM | 14.00 | 16.00 | −10.00 | 3.00 | 1.15 | 1.25 | 3 | 2 |
| | Clairol: #2 | | | | | | | −1:01 −2:01 +1:03 +2:03 Pig: 1 File: 000 | |
| | L'Oreal: M3 | | | | | | | −1:01 −2:01 +1:03 +2:03 Pig: 0 File: 024 | |
| 5 | B. DARKEST DARK BROWN-WARM | 14.00 | 16.00 | −10.00 | 3.00 | 1.25 | 3.00 | 4 | 2 |
| | Clairol: #3 | | | | | | | −1:01 −2:01 +1:03 +2:03 Pig: 1 File: 000 | |
| | L'Oreal: M4 | | | | | | | −1:01 −2:01 +1:03 +2:03 Pig: 0 File: 024 | |
| 6 | C. DARKER DARK BROWN-COOL | 16.00 | 19.00 | −10.00 | 2.00 | −10.00 | 2.70 | 1 | 3 |
| | Clairol: #3 | | | | | | | −1:02 −2:02 +1:04 +2:04 Pig: 2 File: 031 | |
| | L'Oreal: M4 | | | | | | | −1:02 −2:02 +1:04 +2:04 Pig: 1 File: 031 | |
| 7 | C. DARKER DARK BROWN-BORDER C/W--COOL | 16.00 | 19.00 | −10.00 | 2.00 | 2.70 | 2.95 | 2 | 3 |
| | Clairol: #3 | | | | | | | −1:02 −2:02 +1:04 +2:04 Pig: 2 File: 031 | |
| | L'Oreal: M4 | | | | | | | −1:02 −2:02 +1:04 +2:04 Pig: 1 File: 031 | |
| 8 | C. DARKER DARK BROWN-BORDER C/W--WARM | 16.00 | 19.00 | −10.00 | 2.00 | 2.95 | 3.20 | 3 | 3 |
| | Clairol: #3 | | | | | | | −1:02 −2:02 +1:04 +2:04 Pig: 2 File: 034 | |
| | L'Oreal: M4 | | | | | | | −1:02 −2:02 +1:04 +2:04 Pig: 1 File: 034 | |
| 9 | C. DARKER DARK BROWN-WARM | 16.00 | 19.00 | −10.00 | 2.00 | 3.20 | 10.00 | 4 | 3 |
| | Clairol: #3 | | | | | | | −1:02 −2:02 +1:04 +2:04 Pig: 2 File: 034 | |
| | L'Oreal: M4 | | | | | | | −1:02 −2:02 +1:04 +2:04 Pig: 1 File: 034 | |
| 10 | C. DARKER DARK BROWN (AUBURN TONES)--COOL | 16.00 | 19.00 | 2.00 | 3.00 | −10.00 | 3.20 | 1 | 3 |
| | Clairol: #3 | | | | | | | −1:02 −2:02 +1:04 +2:04 Pig: 2 File: 031 | |
| | L'Oreal: M4 | | | | | | | −1:02 −2:02 +1:04 +2:04 Pig: 1 File: 031 | |
| 11 | C. DARKER DARK BROWN (AUBURN TONES)--WARM | 16.00 | 19.00 | 2.00 | 3.00 | 3.20 | 10.00 | 4 | 3 |
| | Clairol: #3 | | | | | | | −1:02 −2:02 +1:04 +2:04 Pig: 2 File: 034 | |
| | L'Oreal: M4 | | | | | | | −1:02 −2:02 +1:04 +2:04 Pig: 1 File: 034 | |
| 13 | D. BROWN - COOL | 19.00 | 22.00 | 0.00 | 3.50 | −10.00 | 2.95 | 1 | 4 |
| | Clairol: #4 | | | | | | | −1:03 −2:03 +1:05 +2:05 Pig: 2 File: 041 | |
| | L'Oreal: M5 | | | | | | | −1:03 −2:03 +1:05 +2:05 Pig: 2 File: 041 | |
| 14 | D. BROWN-BORDER C/W--COOL | 19.00 | 22.00 | 0.00 | 3.50 | 2.95 | 3.20 | 2 | 4 |
| | Clairol: #4 | | | | | | | −1:03 −2:03 +1:05 +2:05 Pig: 2 File: 041 | |
| | L'Oreal: M5 | | | | | | | −1:03 −2:03 +1:05 +2:05 Pig: 2 File: 041 | |
| 15 | D. BROWN-BORDER C/W--WARM | 19.00 | 22.00 | 0.00 | 3.50 | 3.20 | 3.45 | 3 | 4 |
| | Clairol: #4 | | | | | | | −1:03 −2:03 +1:05 +2:05 Pig: 2 File: 044 | |
| | L'Oreal: M5 | | | | | | | −1:03 −2:03 +1:05 +2:05 Pig: 2 File: 044 | |
| 16 | D. BROWN-WARM | 19.00 | 22.00 | 0.00 | 3.50 | 3.45 | 10.00 | 4 | 4 |
| | Clairol: #4 | | | | | | | −1:03 −2:03 +1:05 +2:05 Pig: 2 File: 044 | |
| | L'Oreal: M5 | | | | | | | −1:03 −2:03 +1:05 +2:05 Pig: 2 File: 044 | |
| 17 | D. BROWN (AUBURN TONES)-COOL | 19.00 | 22.00 | 3.50 | 6.00 | −10.00 | 3.45 | 1 | 4 |
| | Clairol: #4 | | | | | | | −1:03 −2:03 +1:05 +2:05 Pig: 2 File: 041 | |
| | L'Oreal: M5 | | | | | | | −1:03 −2:03 +1:05 +2:05 Pig: 2 File: 041 | |
| 18 | D. BROWN (AUBURN TONES)-WARM | 19.00 | 22.00 | 3.50 | 6.00 | 3.45 | 10.00 | 4 | 4 |
| | Clairol: #4 | | | | | | | −1:03 −2:03 +1:05 +2:05 Pig: 2 File: 044 | |
| | L'Oreal: M5 | | | | | | | −1:03 −2:03 +1:05 +2:05 Pig: 2 File: 044 | |
| 19 | E. MEDIUM BROWN-COOL | 22.00 | 27.00 | 1.00 | 3.50 | −10.00 | 3.75 | 1 | 5 |
| | Clairol: #5 | | | | | | | −1:04 −2:04 +1:06 +2:06 Pig: 3 File: 051 | |
| | L'Oreal: M6 | | | | | | | −1:04 −2:04 +1:06 +2:06 Pig: 3 File: 051 | |
| 20 | E. MEDIUM BROWN-BORDER C/W--COOL | 22.00 | 27.00 | 1.00 | 3.50 | 3.75 | 4.00 | 2 | 5 |
| | Clairol: #5 | | | | | | | −1:04 −2:04 +1:06 +2:06 Pig: 3 File: 051 | |
| | L'Oreal: M6 | | | | | | | −1:04 −2:04 +1:06 +2:06 Pig: 3 File: 051 | |
| 21 | E. MEDIUM BROWN (G)-BORDER C/W--WARM | 22.00 | 27.00 | 1.00 | 3.50 | 4.00 | 4.25 | 3 | 5 |
| | Clairol: #5 | | | | | | | −1:04 −2:04 +1:06 +2:06 Pig: 3 File: 054 | |
| | L'Oreal: M6 | | | | | | | −1:04 −2:04 +1:06 +2:06 Pig: 3 File: 054 | |
| 22 | E. MEDIUM BROWN (G)-WARM | 22.00 | 27.00 | 1.00 | 3.50 | 4.25 | 10.00 | 4 | 5 |
| | Clairol: #5 | | | | | | | −1:04 −2:04 +1:06 +2:06 Pig: 3 File: 054 | |
| | L'Oreal: M6 | | | | | | | −1:04 −2:04 +1:06 +2:06 Pig: 3 File: 054 | |
| 23 | E. MEDIUM BROWN (AUBURN TONES)-C-COOL | 22.00 | 27.00 | 3.50 | 6.00 | −10.00 | 4.25 | 1 | 5 |
| | Clairol: #5 | | | | | | | −1:04 −2:04 +1:06 +2:06 Pig: 3 File: 051 | |
| | L'Oreal: M6 | | | | | | | −1:04 −2:04 +1:06 +2:06 Pig: 3 File: 051 | |
| 24 | E. MEDIUM BROWN (AUBURN TONES)-WARM | 22.00 | 27.00 | 3.50 | 6.00 | 4.25 | 10.00 | 4 | 5 |
| | Clairol: #5 | | | | | | | −1:04 −2:04 +1:06 +2:06 Pig: 3 File: 054 | |
| | L'Oreal: M6 | | | | | | | −1:04 −2:04 +1:06 +2:06 Pig: 3 File: 054 | |
| 25 | F. DARKEST MEDIUM BLONDE-COOL | 27.00 | 28.00 | 1.80 | 6.00 | −5.00 | 6.00 | 1 | 6 |
| | Clairol: #6 | | | | | | | 1:05 −2:05 +1:07 +2:07 Pig: 4 File: 061 | |
| | L'Oreal: M7 | | | | | | | −1:05 −2:05 +1:07 +2:07 Pig: 4 File: 061 | |
| 26 | F. DARKEST MEDIUM BLONDE-BORDER C/W--COOL | 27.00 | 28.00 | 1.80 | 5.00 | 6.00 | 6.50 | 2 | 6 |
| | Clairol: #6 | | | | | | | −1:05 −2:05 +1:07 +2:07 Pig: 4 File: 061 | |
| | L'Oreal: M7 | | | | | | | −1:05 −2:05 +1:07 +2:07 Pig: 4 File: 061 | |

TABLE IV-continued

| | Category Name | DATABASE LMin | LMax | aMin | aMax | bMin | bMax | CW | Level |
|---|---|---|---|---|---|---|---|---|---|
| 27 | F. DARKEST MEDIUM BLONDE-BORDER C/W-WARM | 27.00 | 28.00 | 5.00 | 6.00 | 6.00 | 6.50 | 3 | 6 |
| | Clairol: #6 | | | | | −1:05 −2:05 +1:07 +2:07 Pig: 4 File: 064 | | | |
| | L'Oreal: M7 | | | | | −1:05 −2:05 +1:07 +2:07 Pig: 4 File: 064 | | | |
| 28 | F. DARKEST MEDIUM BLONDE-WARM | 27.00 | 28.00 | 1.80 | 6.00 | 6.50 | 15.00 | 4 | 6 |
| | Clairol: #6 | | | | | −1:05 −2:05 +1:07 +2:07 Pig: 4 File: 064 | | | |
| | L'Oreal: M7 | | | | | −1:05 −2:05 +1:07 +2:07 Pig: 4 File: 064 | | | |
| 29 | G. MEDIUM BLONDE-COOL | 28.00 | 31.00 | 1.80 | 6.00 | −5.00 | 6.00 | 1 | 7 |
| | Clairol: #6 | | | | | −1:06 −2:06 +1:08 +2:08 Pig: 4 File: 071 | | | |
| | L'Oreal: M8 | | | | | −1:06 −2:06 +1:08 +2:08 Pig: 5 File: 071 | | | |
| 30 | G. MEDIUM BLONDE-BORDER C/W--COOL | 28.00 | 31.00 | 1.80 | 5.00 | 6.00 | 6.50 | 2 | 7 |
| | Clairol: #6 | | | | | −1:06 −2:06 +1:08 +2:08 Pig: 4 File: 071 | | | |
| | L'Oreal: M8 | | | | | −1:06 −2:06 +1:08 +2:08 Pig: 5 File: 071 | | | |
| 31 | G. MEDIUM BLONDE (G)-BORDER C/W--WARM | 28.00 | 31.00 | 5.00 | 6.00 | 6.00 | 6.50 | 3 | 7 |
| | Clairol: #6 | | | | | −1:06 −2:06 +1:08 +2:08 Pig: 4 File: 074 | | | |
| | L'Oreal: M8 | | | | | −1:06 −2:06 +1:08 +2:08 Pig: 5 File: 074 | | | |
| 32 | G. MEDIUM BLONDE (G)-WARM | 28.00 | 31.00 | 1.80 | 6.00 | 6.50 | 15.00 | 4 | 7 |
| | Clairol: #6 | | | | | −1:06 −2:06 +1:08 +2:08 Pig: 4 File: 074 | | | |
| | L'Oreal: M8 | | | | | −1:06 −2:06 +1:08 +2:08 Pig: 5 File: 074 | | | |
| 33 | H. LIGHTEST MEDIUM BLONDE-COOL | 31.00 | 33.00 | 1.80 | 6.00 | −5.00 | 6.00 | 1 | 8 |
| | Clairol: #7 | | | | | −1:07 −2:07 +1:09 +2:09 Pig: 5 File: 081 | | | |
| | L'Oreal: M8 | | | | | −1:07 −2:07 +1:09 +2:09 Pig: 5 File: 081 | | | |
| 34 | H. LIGHTEST MEDIUM BLONDE-BORDER C/W--COOL | 31.00 | 33.00 | 1.80 | 5.00 | 6.00 | 6.50 | 2 | 8 |
| | Clairol: #7 | | | | | −1:07 −2:07 +1:09 +2:09 Pig: 5 File: 081 | | | |
| | L'Oreal: M8 | | | | | −1:07 −2:07 +1:09 +2:09 Pig: 5 File: 081 | | | |
| 35 | H. LIGHTEST MEDIUM BLONDE-BORDER C/W--WARM | 31.00 | 33.00 | 5.00 | 6.00 | 6.00 | 6.50 | 3 | 8 |
| | Clairol: #7 | | | | | −1:07 −2:07 +1:09 +2:09 Pig: 5 File: 084 | | | |
| | L'Oreal: M8 | | | | | −1:07 −2:07 +1:09 +2:09 Pig: 5 File: 084 | | | |
| 36 | H. LIGHTEST MEDIUM BLONDE-WARM | 31.00 | 33.00 | 1.80 | 6.00 | 6.50 | 15.00 | 4 | 8 |
| | Clairol: #7 | | | | | −1:07 −2:07 +1:09 +2:09 Pig: 5 File: 084 | | | |
| | L'Oreal: M8 | | | | | −1:07 −2:07 +1:09 +2:09 Pig: 5 File: 084 | | | |
| 37 | I. LIGHT BLONDE-COOL | 33.00 | 36.00 | 1.80 | 6.00 | −5.00 | 7.00 | 1 | 9 |
| | Clairol: #7 | | | | | −1:08 −2:08 +1:10 +2:10 Pig: 5 File: 091 | | | |
| | L'Oreal: M9 | | | | | −1:08 −2:08 +1:10 +2:10 Pig: 6 File: 091 | | | |
| 38 | I. LIGHT BLONDE-BORDER C/W--COOL | 33.00 | 36.00 | 1.80 | 5.00 | 7.00 | 7.50 | 2 | 9 |
| | Clairol: #7 | | | | | −1:08 −2:08 +1:10 +2:10 Pig: 5 File: 091 | | | |
| | L'Oreal: M9 | | | | | −1:08 −2:08 +1:10 +2:10 Pig: 6 File: 091 | | | |
| 39 | I. LIGHT BLONDE-BORDER C/W--WARM | 33.00 | 36.00 | 5.00 | 6.00 | 7.00 | 7.50 | 3 | 9 |
| | Clairol: #7 | | | | | −1:08 −2:08 +1:10 +2:10 Pig: 5 File: 094 | | | |
| | L'Oreal: M9 | | | | | −1:08 −2:08 +1:10 +2:10 Pig: 6 File: 094 | | | |
| 40 | I. LIGHT BLONDE-WARM | 33.00 | 36.00 | 1.80 | 6.00 | 7.50 | 20.00 | 4 | 9 |
| | Clairol: #7 | | | | | −1:08 −2:08 +1:10 +2:10 Pig: 5 File: 094 | | | |
| | L'Oreal: M9 | | | | | −1:08 −2:08 +1:10 +2:10 Pig: 6 File: 094 | | | |
| 41 | J. LIGHTER BLONDE-COOL | 36.00 | 40.00 | 1.80 | 6.00 | −5.00 | 8.00 | 1 | 10 |
| | Clairol: #8 | | | | | −1:09 −2:09 +1:11 +2:11 Pig: 6 File: 101 | | | |
| | L'Oreal: M9 | | | | | −1:09 −2:09 +1:11 +2:11 Pig: 6 File: 101 | | | |
| 42 | J. LIGHTER BLONDE-BORDER C/W--COOL | 36.00 | 40.00 | 1.80 | 5.00 | 8.00 | 8.50 | 2 | 10 |
| | Clairol: #8 | | | | | −1:09 −2:09 +1:11 +2:11 Pig: 6 File: 101 | | | |
| | L'Oreal: M9 | | | | | −1:09 −2:09 +1:11 +2:11 Pig: 6 File: 101 | | | |
| 43 | J. LIGHTER BLONDE-BORDER C/W--WARM | 36.00 | 40.00 | 5.00 | 6.00 | 8.00 | 8.50 | 3 | 10 |
| | Clairol: #8 | | | | | −1:09 −2:09 +1:11 +2:11 Pig: 6 File: 104 | | | |
| | L'Oreal: M9 | | | | | −1:09 −2:09 +1:11 +2:11 Pig: 6 File: 104 | | | |
| 44 | J. LIGHTER BLONDE-WARM | 36.00 | 40.00 | 1.80 | 6.00 | 8.50 | 20.00 | 4 | 10 |
| | Clairol: #8 | | | | | −1:09 −2:09 +1:11 +2:11 Pig: 6 File: 104 | | | |
| | L'Oreal: M9 | | | | | −1:09 −2:09 +1:11 +2:11 Pig: 6 File: 104 | | | |
| 45 | K. LIGHTEST BLONDE-COOL | 40.00 | 50.00 | 1.80 | 7.00 | −5.00 | 9.00 | 1 | 11 |
| | Clairol: #9 | | | | | −1:10 −2:10 +1:11 +2:11 Pig: 8 File: 111 | | | |
| | L'Oreal: M10 | | | | | −1:10 −2:10 +1:11 +2:11 Pig: 6 File: 111 | | | |
| 46 | K. LIGHTEST BLONDE-BORDER C/W--COOL | 40.00 | 50.00 | 1.80 | 5.00 | 9.00 | 10.00 | 2 | 11 |
| | Clairol: #9 | | | | | −1:10 −2:10 +1:11 +2:11 Pig: 8 File: 111 | | | |
| | L'Oreal: M10 | | | | | −1:10 −2:10 +1:11 +2:11 Pig: 6 File: 111 | | | |
| 47 | K. LIGHTEST BLONDE-BORDER C/W--WARM | 40.00 | 50.00 | 5.00 | 7.00 | 9.00 | 10.00 | 3 | 11 |
| | Clairol: #9 | | | | | −1:10 −2:10 +1:11 +2:11 Pig: 8 File: 114 | | | |
| | L'Oreal: M10 | | | | | −1:10 −2:10 +1:11 +2:11 Pig: 6 File: 114 | | | |
| 48 | K. LIGHTEST BLONDE-WARM | 40.00 | 50.00 | 1.80 | 7.00 | 10.00 | 30.00 | 4 | 11 |
| | Clairol: #9 | | | | | −1:10 −2:10 +1:11 +2:11 Pig: 8 File: 114 | | | |
| | L'Oreal: M10 | | | | | −1:10 −2:10 +1:11 +2:11 Pig: 6 File: 114 | | | |
| 49 | L. LIGHTEST BLONDE-COOL | 50.00 | 80.00 | 1.80 | 7.00 | −5.00 | 9.00 | 1 | 12 |
| | Clairol: #10 | | | | | −1:10 −2:10 +1:12 +2:12 Pig: 8 File: 111 | | | |
| | L'Oreal: M10 | | | | | −1:10 −2:10 +1:12 +2:12 Pig: 6 File: 111 | | | |
| 50 | L. LIGHTEST BLONDE-BORDER C/W--COOL | 50.00 | 80.00 | 1.80 | 5.00 | 9.00 | 10.00 | 2 | 12 |
| | Clairol: #10 | | | | | −1:10 −2:10 +1:12 +2:12 Pig: 8 File: 111 | | | |
| | L'Oreal: M10 | | | | | −1:10 −2:10 +1:12 +2:12 Pig: 6 File: 111 | | | |

TABLE IV-continued

| | Category Name | DATABASE LMin | LMax | aMin | aMax | bMin | bMax | CW | Level |
|---|---|---|---|---|---|---|---|---|---|
| 51 | L. LIGHTEST BLONDE-BORDER C/W--WARM | 50.00 | 80.00 | 5.00 | 7.00 | 9.00 | 10.00 | 3 | 12 |
| | Clairol: #10 | | | | | −1:10 −2:10 +1:12 +2:12 Pig: 8 File: 114 | | | |
| | L'Oreal: M10 | | | | | −1:10 −2:10 +1:12 +2:12 Pig: 6 File: 114 | | | |
| 52 | L. LIGHTEST BLONDE-WARM | 50.00 | 80.00 | 1.80 | 7.00 | 10.00 | 30.00 | 4 | 12 |
| | Clairol: #10 | | | | | −1:10 −2:10 +1:12 +2:12 Pig: 8 File: 114 | | | |
| | L'Oreal: M10 | | | | | −1:10 −2:10 +1:12 +2:12 Pig: 6 File: 114 | | | |
| 53 | M. LIGHT RED-COOL | 22.00 | 28.00 | 6.00 | 30.00 | −5.00 | 3.50 | 1 | 13 |
| | Clairol: #5 (with Red Violet, Neutral or Blue Violet tones) | | | | | −1:14 −2:14 +1:07 +2:07 Pig: 3 File: 131 | | | |
| | L'Oreal: M6 (with Ash, Iridescent or Auburn tones) | | | | | −1:14 −2:14 +1:07 +2:07 Pig: 3 File: 131 | | | |
| 54 | M. LIGHT RED-BORDER C/W--COOL | 22.00 | 28.00 | 6.00 | 30.00 | 3.50 | 3.75 | 2 | 13 |
| | Clairol: #5 (with Red Violet, Neutral or Blue Violet tones) | | | | | −1:14 −2:14 +1:07 +2:07 Pig: 3 File: 131 | | | |
| | L'Oreal: M6 (with Ash, Iridescent or Auburn tones) | | | | | −1:14 −2:14 +1:07 +2:07 Pig: 3 File: 131 | | | |
| 55 | M. LIGHT RED-BORDER C/W--WARM | 22.00 | 28.00 | 6.00 | 30.00 | 1.75 | 4.00 | 3 | 13 |
| | Clairol: #5 (with Red, Gold or Red Orange tones) | | | | | −1:14 −2:14 +1:07 +2:07 Pig: 3 File: 134 | | | |
| | L'Oreal: M6 (with Gold or Copper tones) | | | | | −1:14 −2:14 +1:07 +2:07 Pig: 3 File: 134 | | | |
| 56 | M. LIGHT RED-WARM | 22.00 | 28.00 | 6.00 | 30.00 | 4.00 | 30.00 | 4 | 13 |
| | Clairol: #5 (with Red, Gold or Red Orange tones) | | | | | −1:14 −2:14 +1:07 +2:07 Pig: 3 File: 134 | | | |
| | L'Oreal: M6 (with Gold or Copper tones) | | | | | −1:14 −2:14 +1:07 +2:07 Pig: 3 File: 134 | | | |
| 57 | N. MEDIUM RED-COOL | 19.00 | 22.00 | 6.00 | 30.00 | −10.00 | 3.50 | 1 | 14 |
| | Clairol: #4 (with Red Violet, Neutral or Blue Violet tones) | | | | | −1:15 −2:15 +1:13 +2:13 Pig: 2 File: 141 | | | |
| | L'Oreal: M5 (with Ash, Iridescent or Auburn tones) | | | | | −1:15 −2:15 +1:13 +2:13 Pig: 2 File: 141 | | | |
| 59 | N. MEDIUM RED-BORDER C/W--COOL | 19.00 | 22.00 | 6.00 | 30.00 | 3.50 | 3.75 | 2 | 14 |
| | Clairol: #4 (with Red Violet, Neutral or Blue Violet tones) | | | | | −1:15 −2:15 +1:13 +2:13 Pig: 2 File: 141 | | | |
| | L'Oreal: M5 (with Ash, Iridescent or Auburn tones) | | | | | −1:15 −2:15 +1:13 +2:13 Pig: 2 File: 141 | | | |
| 59 | N. MEDIUM RED (G)-BORDER C/W--WARM | 19.00 | 22.00 | 6.00 | 30.00 | 3.75 | 4.00 | 3 | 14 |
| | Clairol: #4 (with Red, Gold or Red Orange tones) | | | | | −1:15 −2:15 +1:13 +2:13 Pig: 2 File: 144 | | | |
| | L'Oreal: M5 (with Gold or Copper tones) | | | | | −1:15 −2:15 +1:13 +2:13 Pig: 2 File: 144 | | | |
| 60 | N. MEDIUM RED (G)-WARM | 19.00 | 22.00 | 6.00 | 30.00 | 4.00 | 30.00 | 4 | 14 |
| | Clairol: #4 (with Red, Gold or Red Orange tones) | | | | | −1:15 −2:15 +1:13 +2:13 Pig: 2 File: 144 | | | |
| | L'Oreal: M5 (with Gold or Copper tones) | | | | | −1:15 −2:15 +1:13 +2:13 Pig: 2 File: 144 | | | |
| 61 | O. DARK RED-COOL | 14.00 | 19.00 | 3.00 | 30.00 | −10.00 | 2.50 | 1 | 15 |
| | Clairol: #2/#3 (with Red Violet, Neutral or Blue Violet tones) | | | | | −1:03 −2:03 +1:14 +2:14 Pig: 2 File: 151 | | | |
| | L'Oreal: M4 (with Ash, Iridescent or Auburn tones) | | | | | −1:03 −2:03 +1:14 +2:14 Pig: 2 File: 151 | | | |
| 62 | O. DARK RED-BORDER C/W--COOL | 14.00 | 19.00 | 3.00 | 30.00 | 2.50 | 2.75 | 2 | 15 |
| | Clairol: #2/#3 (with Red Violet, Neutral or Blue Violet tones) | | | | | −1:03 −2:03 +1:14 +2:14 Pig: 2 File: 151 | | | |
| | L'Oreal: M4 (with Ash, Iridescent or Auburn tones) | | | | | −1:03 −2:03 +1:14 +2:14 Pig: 2 File: 151 | | | |
| 63 | O. DARK RED-BORDER C/W--WARM | 14.00 | 19.00 | 3.00 | 30.00 | 2.75 | 3.00 | 3 | 15 |
| | Clairol: #2/#3 (with Red, Gold or Red Orange tones) | | | | | −1:03 −2:03 +1:14 +2:14 Pig: 2 File: 000 | | | |
| | L'Oreal: M4 (with Gold or Copper tones) | | | | | −1:03 −2:03 +1:14 +2:14 Pig: 2 File: 151 | | | |
| 64 | O. DARK RED-WARM | 14.00 | 19.00 | 3.00 | 30.00 | 3.00 | 30.00 | 4 | 15 |
| | Clairol: #2/#3 (with Red, Gold or Red Orange tones) | | | | | −1:03 −2:03 +1:14 +2:14 Pig: 2 File: 000 | | | |
| | L'Oreal: M4 (with Gold or Copper tones) | | | | | −1:03 −2:03 +1:14 +2:14 Pig: 2 File: 151 | | | |
| 65 | P. RED BLONDE | 27.00 | 40.00 | 6.00 | 30.00 | 6.00 | 30.00 | 4 | 16 |
| | Clairol: #6/#7/#8 (with Red, Gold or Red Orange tones) | | | | | −1:13 −2:13 +1:18 +2:18 Pig: 7 File: 164 | | | |
| | L'Oreal: M7/M8 (with Gold or Copper tones) | | | | | −1:13 −2:13 +1:18 +2:18 Pig: 5 File: 164 | | | |
| 66 | Q. RED BLONDE | 40.00 | 50.00 | 7.00 | 30.00 | 6.00 | 30.00 | 4 | 17 |
| | Clairol: #9/#10 (with Red, Gold or Red Orange tones) | | | | | −1:16 −2:16 +1:11 +2:11 Pig: 7 File: 164 | | | |
| | L'Oreal: M7/M8 (with Gold or Copper tones) | | | | | −1:16 −2:16 +1:11 +2:11 Pig: 6 File: 164 | | | |
| 67 | R. RED BLONDE | 50.00 | 80.00 | 7.00 | 30.00 | 6.00 | 30.00 | 4 | 18 |
| | Clairol: #9/#10 (with Red, Gold or Red Orange tones) | | | | | −1:16 −2:16 +1:12 +2:12 Pig: 8 File: 164 | | | |
| | L'Oreal: M7/M8 (with Gold or Copper tones) | | | | | −1:16 −2:16 +1:12 +2:12 Pig: 6 File: 164 | | | |
| 68 | S. BLACK/DARK BROWN/MEDIUM BROWN/BROWN WITH 70%–90% GREY HAIR-WARM | 27.00 | 50.00 | −10.00 | 1.80 | 4.25 | 10.00 | 4 | 19 |
| | Clairol: | | | | | −1:01 −2:01 +1:03 +2:03 Pig: 0 File: 000 | | | |
| | L'Oreal: | | | | | −1:01 −2:01 +1:03 +2:03 Pig: 0 File: 024 | | | |
| 69 | S. BLACK/DARK BROWN/MEDIUM BROWN/BROWN WITH 70%–90% GREY HAIR-BORDER C/W--WARM | 27.00 | 50.00 | −10.00 | 1.80 | 4.00 | 4.25 | 3 | 19 |
| | Clairol: | | | | | −1:01 −2:01 +1:03 +2:03 Pig: 0 File: 000 | | | |
| | L'Oreal: | | | | | −1:01 −2:01 +1:03 +2:03 Pig: 0 File: 024 | | | |
| 70 | S. BLACK/DARK BROWN/MEDIUM BROWN/BROWN WITH 70%–90% GREY HAIR-BORDER C/W--COOL | 27.00 | 50.00 | −10.00 | 1.80 | 3.75 | 4.00 | 2 | 19 |
| | Clairol: | | | | | −1:01 −2:01 +1:03 +2:03 Pig: 0 File: 021 | | | |
| | L'Oreal: | | | | | −1:01 −2:01 +1:03 +2:03 Pig: 0 File: 021 | | | |
| 71 | S. BLACK/DARK BROWN/MEDIUM BROWN/BROWN WITH 70%–90% GREY HAIR-COOL | 27.00 | 50.00 | −10.00 | 1.80 | −10.00 | 3.75 | 1 | 19 |
| | Clairol: | | | | | −1:01 −2:01 +1:03 +2:03 Pig: 0 File: 021 | | | |
| | L'Oreal: | | | | | −1:01 −2:01 +1:03 +2:03 Pig: 0 File: 021 | | | |
| 72 | T. BLACK/DARK BROWN/MEDIUM BROWN/BROWN WITH 40%–60% GREY HAIR-WARM | 23.00 | 27.00 | −10.00 | 1.00 | 4.25 | 10.00 | 4 | 20 |
| | Clairol: | | | | | −1:01 −2:01 +1:03 +2:03 Pig: 0 File: 000 | | | |
| | L'Oreal: | | | | | −1:01 −2:01 +1:03 +2:03 Pig: 0 File: 024 | | | |
| 73 | T. BLACK/DARK BROWN/MEDIUM BROWN/BROWN WITH 40%–60% GREY HAIR-BORDER C/W--WARM | 23.00 | 27.00 | −10.00 | 1.00 | 4.00 | 4.25 | 3 | 20 |
| | Clairol: | | | | | −1:01 −2:01 +1:03 +2:03 Pig: 0 File: 000 | | | |
| | L'Oreal: | | | | | −1:01 −2:01 +1:03 +2:03 Pig: 0 File: 024 | | | |

TABLE IV-continued

| | Category Name | DATABASE LMin | LMax | aMin | aMax | bMin | bMax | CW | Level |
|---|---|---|---|---|---|---|---|---|---|
| 74 | T. BLACK/DARK BROWN/MEDIUM BROWN/BROWN WITH 40%–60% GREY HAIR-BORDER C/W--COOL | 23.00 | 27.00 | −10.00 | 1.00 | 3.75 | 4.25 | 2 | 20 |
| | Clairol: | | | | | −1:01 −2:01 +1:03 +2:03 Pig: 0 File: 021 | | | |
| | L'Oreal: | | | | | −1:01 −2:01 +1:03 +2:03 Pig: 0 File: 021 | | | |
| 75 | T. BLACK/DARK BROWN/MEDIUM BROWN/BROWN WITH 40%–60% GREY HAIR-COOL | 23.00 | 27.00 | −10.00 | 1.00 | −10.00 | 3.75 | 1 | 20 |
| | Clairol: | | | | | −1:01 −2:01 +1:03 +2:03 Pig: 0 File: 021 | | | |
| | L'Oreal: | | | | | −1:01 −2:01 +1:03 +2:03 Pig: 0 File: 021 | | | |

The menu of hair color action choices available in step 6 are shown in Table III.

The database used in step 7 to arrive at a particular product that will effect the chosen hair color option for the particular person's hair category is shown in Table IV. Certain codes in this appendix that are used by this database require explanation. The same 75 hair color categories 1, 2, 3, 4, etc., and category names as appear in the table are listed under the heading "Category Name." Also under the heading "Category Name," Group, A, B, C, D, etc. is designated as in the table. Next, the ranges of Hunter L, a and b defining the category appear. Under the heading "CW" one of four levels of cool to warm is listed. In these the numeral "1" is coolest, "2" is a border color on the cool side of the cool-warm boundary, "3" is a warm color on the warm side of the cool-warm boundary, and "4" is a warm color. The "Level" column lists again the product manufacturer's "Level" designations like those listed in Table II.

In Table IV database, two manufacturers are listed for each category. Opposite each appears a series of numbers such as −1:01 −2:01 +1:02 +2:02. In each of these numbers the first digit represents an action which may be chosen from the menu of hair color options. For example in −1:01, the number "−1" means making hair color slightly darker. The number "−2" means "darker," which is somewhat more darkening than "slightly darker." The number "+1" means "slightly lighter" and the number "+2" means "lighter," e.g. somewhat more lightening than "slightly lighter." The number after the (:), "01," is a direction to go to category group A. In category Group A, then, are identified the manufacturers products of :011. An index, Table V (set forth below), identifies products of each manufacturer. These are the products that will have the desired effect.

TABLE V

MANUFACTURERS PRODUCTS

CLAIROL FILES

011:

| | |
|---|---|
| Logics Violet | 1V Black |
| Miss Clairol | 82N Dk. Neutral Brown |
| Miss Clairol | 52D Black Azure |
| Miss Clairol | 51D Black Velvet |

014:

| | |
|---|---|
| Logics Blue | 3B Medium Brown |
| Miss Clairol | 84N Lt Neutrl Brown |
| Logics Violet | 3V Medium Brown |
| Miss Clairol | 39G Sunset Brown |
| Miss Clairol | 95D-N Nightfall Brown |
| Miss Clairol | 4D Chestnut Brown |
| Loving Care | 80 Auburn |
| Miss Clairol | 56R Cinnamon |

TABLE V-continued

MANUFACTURERS PRODUCTS

| | |
|---|---|
| Miss Clairol | 37D Iced Brown |

021:

| | |
|---|---|
| Logics Violet | 2V Dark Brown |
| Logics Neutral | 2N Dark Brown |
| Logics Red Violet | 2RV Deep |
| Miss Clairol | 57D Coffee Brown |
| Miss Clairol | 48D Sable Brown |

031:

| | |
|---|---|
| Logics Blue | 3B Medium Brown |
| Logics Neutral | 3N Medium Brown |
| Logics Red Violet | 3RV Medium |
| Logics Violet | 3V Medium Brown |
| Loving Care | 79 Dark Brown |

034:

| | |
|---|---|
| Logics Gold | 3G Medium Brown |

041:

| | |
|---|---|
| Logics Blue | 4B Light Brown |
| Logics Violet | 4V Light Brown |
| Logics Red Violet | 4RV Light |
| Logics Neutral | 4N Light Brown |
| Miss Clairol | 84N Lt Neutrl Brown |
| Miss Clairol | 39G Sunset Brown |
| Miss Clairol | 95D-N Nightfall Brown |
| Miss Clairol | 46D Chestnut Brown |
| Loving Care | 80 Auburn |
| Miss Clairol | 56R Cinnamon |
| Miss Clairol | 37D Iced Brown |

044:

| | |
|---|---|
| Logics Gold | 4G Light Brown |
| Logics Red Orange | 4RO Deep Bright |
| Loving Care | 77 Medium Ash Brown |
| Miss Clairol | 75R Sunsparked Brown |
| Miss Clairol | 47R Red Ginger |
| Loving Care | 83 Natural Black |
| Miss Clairol | 46D Chestnut Brown |
| Loving Care | 60 Auburn |
| Miss Clairol | 56R Cinnamon |
| Loving Care | 82 Dark Warm Brown |
| Miss Clairol | 37D Iced Brown |

051:

| | |
|---|---|
| Logics Neutral | 5N Lightest Brown |
| Logics Violet | 5V Lightest Brown |
| Miss Clairol | 94D-N Twilight Brown |
| Miss Clairol | 86N Dk Neutral Brown |
| Born Blonde Toner | 360 Moonlight Mink |
| Miss Clairol | 36D Moonlit Brown |
| Beautiful Browns | 18D Darkest Brown |
| Beautiful Browns | 20D Black |
| Beautiful Browns | 15W Dark Warm Brown |
| Miss Clairol | 32D Moon Haze |

054:

| | |
|---|---|
| Beautiful Browns | 12D Medium Ash Brown |
| Loving Care | 76 Lt Golden Brown |

TABLE V-continued

| MANUFACTURERS | PRODUCTS |
|---|---|
| Cream Toner | 345D True Camel Beige |
| Cream Toner | 346D True Taupe Beige |
| Loving Care | 78 Med Golden Brown |
| Loving Care | 75 Light Ash Brown |
| Loving Care | 74 Reddish Blonde |
| Miss Clairol | 42D Moongold |
| Loving Care | 775 Smokey Ash Brown |
| Miss Clairol | 35G Sunlit Brown |
| Beautiful Browns | 20D Black |
| Beautiful Browns | 15W Dark Warm Brown |
| Miss Clairol | 32D Moon Haze |
| 061: | |
| Beautiful Browns | 11W Med Golden Brown |
| Jazzing | 78 Creme Soda |
| Born Blonde Toner | 354 Baby Blush |
| Creme Toner | 343D True Ash Blonde |
| Born Blonde Toner | 357 Beautiful Beige |
| Beautiful Browns | 131D Med Smokey Brown |
| Miss Clairol | 28D Autumn Mist |
| Miss Clairol | 25G Sunblonde Brown |
| Beautiful Browns | 13W Med Warm Brown |
| Miss Clairol | 74G Sunwashed Blonde |
| Beautiful Browns | 121W Med Honey Brown |
| 064: | |
| Beautiful Browns | 10W Bronzed Brown |
| Miss Clairol | 28D Autumn Mist |
| Miss Clairol | 25G Sunblonde Brown |
| Beautiful Browns | 13W Med Warm Brown |
| Miss Clairol | 74G Sunwashed Blonde |
| Beautiful Browns | 121W Med Honey Brown |
| Beautiful Browns | 131D Med Smokey Brown |
| 071: | |
| Born Blonde Toner | 356 Innocent Ivory |
| Logics Blue | 6V Dark Blonde |
| Born Blonde Toner | 358 Winsome Wheat |
| Beautiful Browns | 8D Light Ash Brown |
| Born Blonde Toner | 355 Blissfully Bonde |
| Jazzing | 76 Sandstorm |
| Born Blonde Toner | 359 Fair Fawn |
| Miss Clairol | 93D-N Dusk Blonde |
| Miss Clairol | 34D Hazy Mist |
| Miss Clairol | 88N Lt Neutral Blnde |
| Miss Clairol | 34D Hazy Mist |
| Creme Toner | 342D True Brown Blonde |
| Creme Toner | 10B Sandy Blonde |
| Creme Toner | 341D True Tan Blonde |
| 074: | |
| Beautiful Blondes | 6D Blonde Brown |
| Miss Clairol | 41G Golden Apricot |
| Beautiful Reds | 9W Lt Reddish Brown |
| Creme Toner | 344R True Tawny Beige |
| Loving Care | 73 Ash Blonde |
| Miss Clairol | 88N Lt Neutral Blnde |
| Miss Clairol | 34D Hazy Mist |
| Creme Toner | 342D True Brown Blnde |
| Creme Toner | 10B Sandy Blonde |
| Creme Toner | 341 True Tan Blonde |
| 081: | |
| Born Blonde Toner | 352 Precious Platnm |
| Born Blonde Toner | 353 Sweet Silver |
| Born Blonde Toner | 361 Happy Honey |
| Jazzing | 72 Icicle |
| Creme Toner | 311D 9A Towhead |
| Creme Toner | 309D Champgn Parfait |
| Creme Toner | 331G Tan Pearl |
| Miss Clairol | 92D-N Daybreak Blonde |
| Logics Violet | 7V Medium Blonde |
| 084: | |
| Beautiful Blondes | 4W Med Golden Blonde |
| Creme Toner | 307D Champagne Ice |
| Logics Gold | 8G Light Blonde |
| Cream Toner | 303G Champgn Beige |
| Loving Care | 72 Golden Blonde |
| Beautiful Brights | 30W 14K Gold |
| Miss Clairol | 27G Spring Honey |
| Beautiful Blondes | 5D Light Ash Blonde |
| Creme Toner | 311D 9A Towhead |
| Creme Toner | 309D Champgn Parfait |
| Cream Toner | 311G Tan Pearl |
| Logics Violet | 7V Medium Blonde |
| Miss Clairol | 92DN Daybreak Blonde |
| Miss Clairol | 71R-G Sunrise Gold |
| 091: | |
| Jazzing | 10 Clear Hairglosser |
| Logics Blue | 8B Light Blonde |
| Born Blonde Toner | 351 Silent Snow |
| Creme Toner | 310D Champgn Toast |
| 094: | |
| Beautiful Blondes | 2W Lt Golden Blonde |
| 101: | |
| Logics Violet | 12V Ultra Lt Blond |
| Miss Clairol | 20D Arctic Blonde |
| Creme Toner | 302D Platinum Beige |
| Creme Toner | 319G Ivory Chiffon |
| Creme Toner | 315G X-Lite B |
| Logics Blue | 12B Ultra Lt Blonde |
| Logics Violet | 8V Light Blonde |
| Miss Clairol | 91D-N Starlit Blonde |
| Creme Toner | 314G x-Lite A |
| Creme Toner | 332R Strawberry Blnde |
| Miss Clairol | 40D Topaz |
| Miss Clairol | 26D Winter Wheat |
| Logics Gold | 10G Lightest Blonde |
| 104: | |
| Creme Toner | 340G True Golden Blonde |
| Creme Toner | 332R Strawberry Blnde |
| Miss Clairol | 40D Topaz |
| Miss Clairol | 26D Winter Wheat |
| Logics Gold | 10G Lightest Blonde |
| 111: | |
| Creme Toner | 301D White Beige |
| Logics Blue | 10B Lightest Blonde |
| Creme Toner | 323D X-Lite Platinum |
| Miss Clairol | 30D Flaxen Blonde |
| Logics Violet | 10V Lightest Blonde |
| Logics Gold | 12G Ultra Lt. Blonde |
| 114: | |
| Miss Clairol | 12G Blondest Blonde |
| Jazzing | 20 Bold Gold |
| Logics Violet | 10V Lightest Blonde |
| Logics Gold | 12G Ultra Lt Blonde |
| 131: | |
| Beautiful Reds | 175W Wine Brown |
| Beautiful Brights | 17W Rosewood Brown |
| Beautiful Brights | 40W Amethyst |
| 134: | |
| Beautiful Reds | 14W Cedar Red Brown |
| Miss Clairol | 33R Flame |
| Miss Clairol | 45R Sparkling Sherry |
| Beautiful Brights | 38W Ruby |
| Logics Red Orange | 4RO Deep Bright |
| Miss Clairol | 44R Coppertone |
| Beautiful Reds | 17W Rosewood Brown |
| 141: | |
| Logics Red Violet | 3RV Medium |
| Logics Red Violet | 4RV Light |
| 144: | |
| Logics Red Violet | 4RV Light |
| Miss Clairol | 64R Red Oak |

TABLE V-continued

MANUFACTURERS PRODUCTS

151:

| | |
|---|---|
| Miss Clairol | 68R Berrywood |
| Miss Clairol | 70R Plum Brown |
| Logics Red Violet | 2RV Deep |

164:

| | |
|---|---|
| Logics Red Orange | 10RO Ltst Bright |
| Logics Red Orange | 8RO Light Bright |
| Miss Clairol | 29R Honey Red |
| Miss Clairol | 43R Sun Bronze |
| Miss Clairol | 72R Sunberry |
| Beautiful Reds | 91W Copper Red |
| Jazzing | 40 Red Hot |
| Beautiful Brights | 34W Spiced Topaz |
| Beautiful Brights | 32W Amber |
| Jazzing | 30 Spiced Cognac |
| Logics Red Orange | 6RO Med Bright |
| Miss Clairol | 31R Sunny Auburn |
| Miss Clairol | 73R-G Apricot Glaze |

L'OREAL FILES

011:

| | |
|---|---|
| Majirel | M1 Black |
| Crescendo | 1 Black |
| Diacolor | Darkest Brown |
| Diacolor | Plum |

021:

| | |
|---|---|
| Crescendo | 3 Darkest Brown |
| Majirel | M3 Darkest Brown |
| Majirel | M5.12 Medium Ash Iridescent Brown |
| Majirel | M4 Dark Brown |

024:

| | |
|---|---|
| Diacolor | Dark Brown |
| Diacolor | Medium Natural Ash Brown |

031:

| | |
|---|---|
| Crescendo | 4 Dark Brown |
| Crescendo | 5.1 Ash Brown |
| Crescendo | 5 Brown |
| Diacolor | Medium Brown |
| Majirel | M6.12 Light Ash Iridescent Brown |
| Majirel | M6.1 Light Ash Brown |
| Majirel | M5.1 Ash Brown |
| Majirel | M5 Brown |

034:

| | |
|---|---|
| Diacolor | Light Brown |
| Diacolor | Light Natural Ash Blonde |
| Majirel | M5 Brown |

041:

| | |
|---|---|
| Crescendo | 5 Brown |
| Majirel | 6.2 Light Iridescent Brown |
| Majirel | M4.51 Ash Mahogany Brown |
| Crescendo | 6 Light Brown |
| Crescendo | 6.01 Light Natural Ash Brown |
| Crescendo | 6.12 Light Ash Iridescent Brown |
| Majirel | M6.23 Light Iridescent Golden Brown |
| Majirel | M5.15 Mahogany Ash Light Brown |
| Crescendo | 5.3 Golden Brown |

044:

| | |
|---|---|
| Diacolor | Dark Blonde |
| Majirel | M5.3 Golden Brown |
| Majirel | M7.01 Dark Natural Ash Blonde |
| Crescendo | 6.52 Lt Mahogany Irid Brown |
| Majirel | M6 Light Brown |
| Majirel | M7.1 Dark Ash Blonde |
| Majirel | M6.01 Light Natural Amber Brown |
| Majirel | M6.23 Light Iridescent Golden Brown |
| Majirel | M5.15 Mahogany Ash Light Brown |
| Crescendo | 5.3 Golden Brown |

051:

| | |
|---|---|
| Majirel | M7.23 Dark Iridescent Golden Blonde |
| Crescendo | 7.01 Dark Natural Ash Blonde |
| Crescendo | 7.1 Dark Ash Blonde |
| Diacolor | Natural Ash |

054:

| | |
|---|---|
| Majirel | Color Mixer Dark Ash |
| Crescendo | 8.31 Golden Ash Blonde |
| Crescendo | 7.31 Dk Golden Ash Blonde |
| Majirel | M6.52 Light Mahogany Irid Brown |
| Majirel | M7 Dark Blonde |
| Crescendo | 7 Dark Blonde |
| Crescendo | 8.52 Mahogany Irid Blonde |
| Crescendo | 8.42 Copper Irid Blonde |

061:

| | |
|---|---|
| Majirel | Color Mixer Light Ash |
| Majirel | M9.01 Natural Ash Blonde |
| Crescendo | 8.13 Ash Beige Blonde |
| Crescendo | 8.01 Natural Ash Blonde |
| Crescendo | 10.1 Very Light Ash Blonde |
| Crescendo | 10.01 Very Light Natural Blonde |
| Crescendo | 9.1 Light Ash Blonde |
| Diacolor | Dark Natural Ash Blonde |
| Crescendo | 9.12 Light Ash Iridescent Blonde |
| Crescendo | 9.13 Light Ash Beige Blonde |

064:

| | |
|---|---|
| Majirel | M7.3 Dark Golden Blonde |
| Majirel | M8.3 Golden Blonde |
| Majirel | M8 Blonde |

071:

| | |
|---|---|
| Majirel | M9.12 Light Ash Iridescent Blonde |
| Crescendo | 9.01 Lt Natural Ash Blonde |
| Majirel | Color Mixer Light Ash |
| Majirel | M8.1 Ash Blonde |
| Crescendo | 8 Blonde |

074:

| | |
|---|---|
| Crescendo | 9.04 Lt Natural Copper Blonde |
| Crescendo | 8.3 Golden Blonde |
| Majirel | M8.1 Ash Blonde |
| Crescendo | 8 Blonde |

081:

| | |
|---|---|
| Crescendo | 10.1 Very Light Ash Blonde |
| Crescendo | 10.01 Very Light Natural Blonde |
| Crescendo | 9.1 Light Ash Blonde |
| Crescendo | 9.12 Light Ash Iridescent Blonde |
| Crescendo | 9.13 Light Ash Beige Blonde |

084:

| | |
|---|---|
| Crescendo | 9.31 Lt Golden Ash Blonde |
| Crescendo | 9 Light Blonde |
| Crescendo | 9.12 Lt Ash Irid Blonde |
| Crescendo | 9.13 Lt Ash Beige Blonde |

091:

| | |
|---|---|
| Majirel | M10.1 Very Lt Ash Blonde |
| Crescendo | P10A Pearl Ash |
| Majirel | M9.01 Lt Natural Ash Blonde |
| Crescendo | 10.21 Very Light Iridescent Ash Blonde |
| Diacolor | Light Beige |
| Majirel | M10.01 Very Light Natural Ash Blonde |
| Crescendo | P10A Shimmer Beige |
| Diacolor | Light Ash Blonde |
| Crescendo | 10 Very Light Blonde |

094:

| | |
|---|---|
| Crescendo | 9.3 Light Golden Blonde |
| Majirel | M9 Light Blonde |
| Majirel | M9.3 Light Golden Blonde |
| Majiblond | 901X Extra Lt Ash Blonde |

TABLE V-continued

| | MANUFACTURERS PRODUCTS |
|---|---|
| Diacolor | Light Beige |
| Majirel | M10.01 Very Light Natural Ash Blonde |
| Crescendo | P10A Shimmer Beige |
| Diacolor | Light Ash Blonde |
| Crescendo | 10 Very Light Blonde |
| 101: | |
| Majiblond | 901 Light Light Natural Ash Blonde |
| Majiblond | Lightest Light Ash Irid Blonde |
| 104: | |
| Majirel | M10 Very Light Blonde |
| Majirel | M9.13 Lt Ash Beige Blonde |
| Majiblond | 900 Lt Lt Natural Blonde |
| Majiblond | 911 Lightest Light Int Ash Blonde |
| 111: | |
| Crescendo | P10E Iridescent Ivory |
| Diacolor | Clear |
| 114: | |
| Majiblond | 913X Lightest Lt Natural Beige Blonde |
| Majiblond | 900X Extra Light Platinum Blonde |
| Diacolor | Clear |
| 131: | |
| Majirel | M6.6 Light Auburn Brown |
| 134: | |
| Majirel | M6.64 Light Auburn Copper Brown |
| Diacolor | Copper |
| Majirel | M6.6 Light Auburn Brown |
| Crescendo | 7.43 Dk Copper Golden Blonde |
| Diacolor | Golden Copper |
| Crescendo | 6.46 Light Copper Auburn Brown |
| 141: | |
| Diacolor | Red Mahogany |
| Diacolor | Dark Auburn |
| Majirel | M7.62 Dark Auburn Iridescent Blonde |
| Diacolor | Auburn |
| Diacolor | Light Auburn |
| 144: | |
| Crescendo | 4.56 Dark Mahogany Auburn Brown |
| Majirel | M7.62 Dark Auburn Irid Blonde |
| Diacolor | Auburn |
| Diacolor | Light Auburn |
| Crescendo | 4.45 Dark Copper Mahogany Brown |
| 151: | |
| Majirel | M5.62 Auburn Iridescent Brown |
| Majirel | M5.20 Int Iridescent Brown |
| 164: | |
| Majirel | M8.34 Golden Copper Blonde |
| Majirel | M9.04 Light Natural Copper Blonde |
| Majirel | M7.4 Dark Copper Blonde |
| Majiblond | 903 Light Light Natural Golden Blonde |
| Majirel | M7.40 Dark Int Copper Blonde |
| Diacolor | Gold |
| Crescendo | 7.44 Dark Tp Copper Blonde |
| Crescendo | 8.34 Golden Copper Blonde |
| Crescendo | 4.56 Dark Mahogany Auburn Blonde |

From the database of Table IV it will be seen, then, that, for example, to darken hair of Categories 2, 3, 4, and 5, "01" appears, making reference to Category Group A1.

The database of Table III was developed empirically by, first, measuring the Hunter L, a and b of an enormous number of sample hairs from the numerous Categories, then applying the colorants of the manufacturers to these hairs and again measuring the Hunter L, a and b to determine the color change effect of the hairs thus colored. This was done as well for the lighter ends of these hairs and for darker roots. This was also done for greying hair for use in the grey hair program described below. In this fashion the database of Table III as built.

Figure 4:
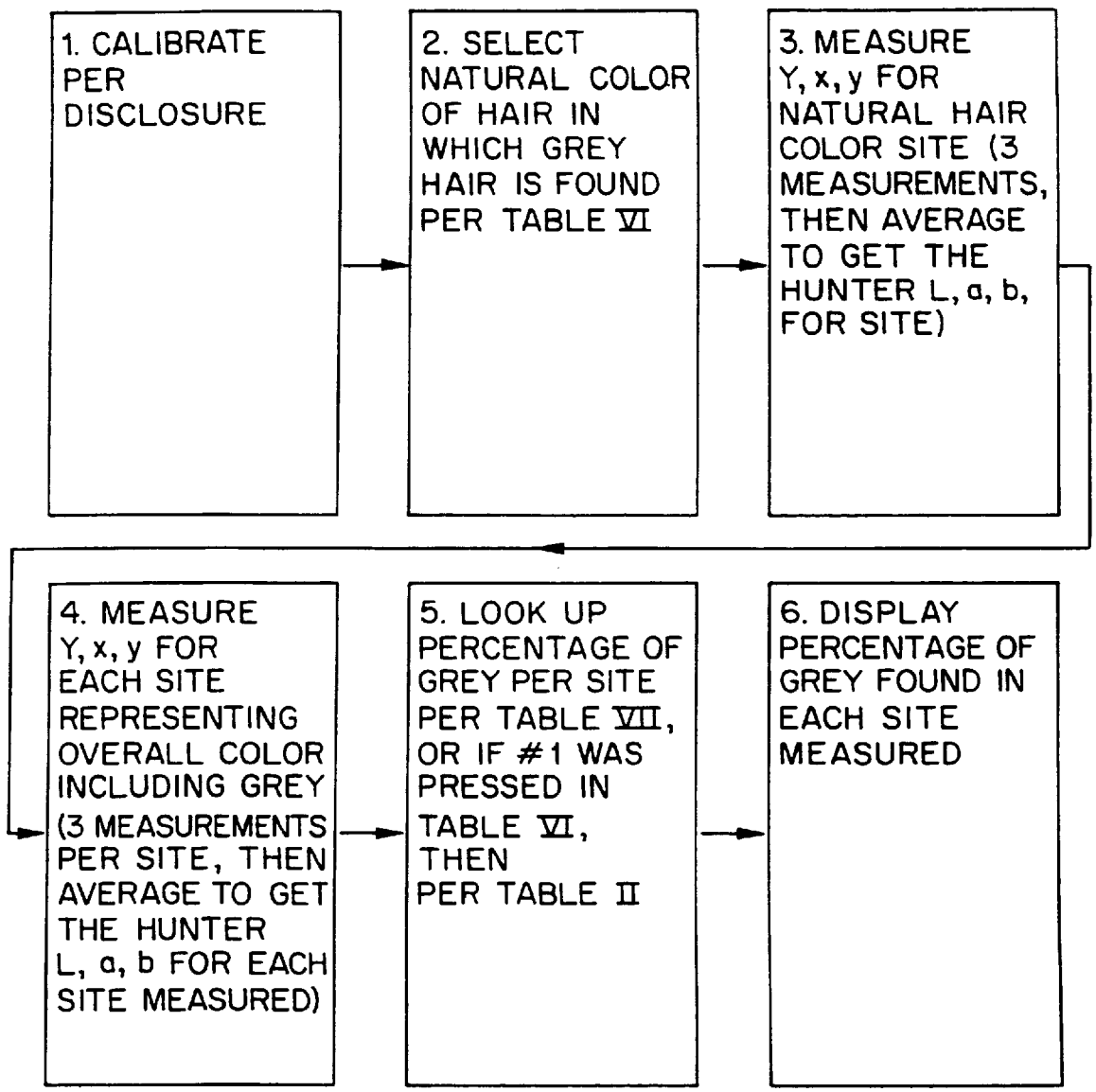
FIG. 4 is a schematic illustration in block diagram form illustrating the steps in the process of arriving at hair color classification of a greying individual.

Turning to the block diagram of FIG. 4 characterization of greying hair can be accomplished, following calibration of the instrument at step one, by selecting one's natural color from the following List Of Natural Hair Color Options by step 2.

TABLE VI

LIST OF NATURAL HAIR COLOR OPTIONS
FOR GREY HAIR PROGRAM

| | |
|---|---|
| 1. | If Grey is present in Black, Dark Brown, Medium Brown or Brown Hair, please press #1. |
| 2. | If Grey is present in Light Brown/Darkest Blonde Hair, please press #2. |
| 3. | If Grey is present in Dark Red, Medium Red or Medium Light Red Hair, please press #3. |
| 4. | If Grey is present in Light Red or Red Blonde Hair, please press #4. |
| 5. | If Grey is present in Medium to Medium Dark Blonde Hair, please press #5. |
| 6. | If Grey is present in Light Blonde Hair, please press #6. |

Again, at step three Y, x and y for the natural hair is identified, either by measurement at a natural hair color site on the individual or by the individual's identifying hair swatches considered to be his or her natural color. From Y, x and y, Hunter L, a and b—three measurements are taken and then averaged to reach average Hunter L, a and b, or in the case of the swatch this may already have been done so that Hunter L, a and b for the swatch is known.

Further sites containing grey are then measured at step 4 to arrive at Y, x and y for these additional sites, which again may be the sides, top, back of the head, roots and ends. The same procedure is followed with three measurements per site to reach average Y, x and y for each site and thereafter calculating average L, a and b for each site. With the Hunter L, a and b for natural hair and the Hunter L, a and b for the greying hair determined, the table entitled Calculation of Percentage of Grey Hair Table VII, set forth below is consulted, which defines the grey hair categories on the basis of percentage of grey (step 5).

The percentage grey thus identified is displayed (step 6) and this represents the category for an individual with greying hair. This characterization is used similarly to the previously described characterization or category of the table of hair categories shown in Table II.

Figure 5:
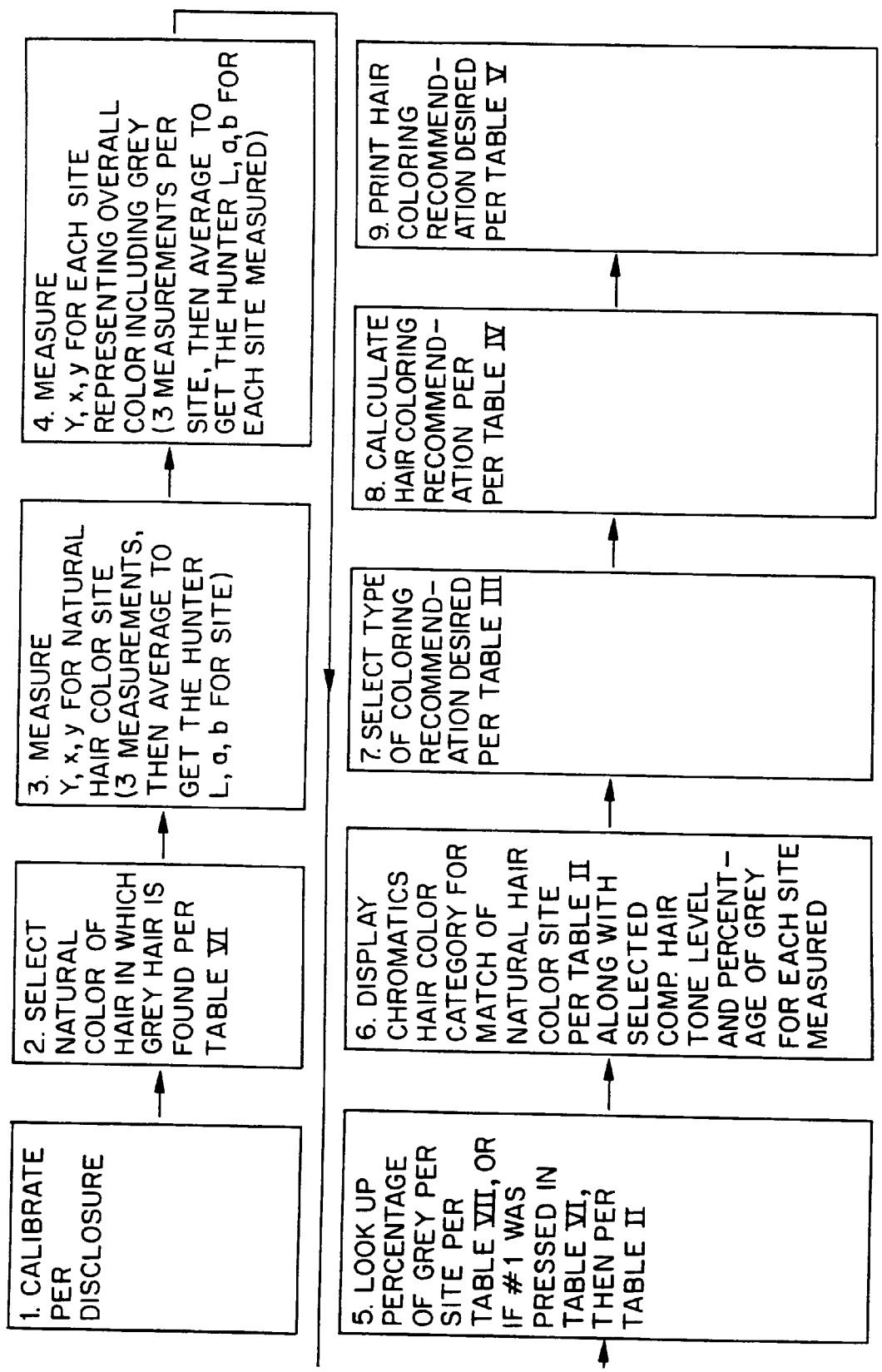
FIG. 5 is a schematic illustration in block diagram form illustrating the steps in the process of using hair color classification of a greying individual and a database to arrive at a coloring agent for making a selected alteration in hair color.

In FIG. 5 the use of the grey hair identification as just described in a procedure for identifying colorants to achieve a desired result is indicated. After calibration of the instrument (step 1) as described above, the steps previously discussed in connection with FIG. 4 are followed to identify the category of greying hair. Then, at step 7 of FIG. 5 from the menu of options appearing above, a selection of one of the 35 choices is made. With that, now the database of Table IV (step 8) can be used in exactly the same manner as described previously. That is to say, the category of hair is found, the option selected is chosen as −1, −2, +1 or +2. The Category Group designator, 01, 02, 03, etc. is used to identify the appropriate category family to go to and in that category family is found the identifier of manufacturer's hair colorants that will produce the desired result which is found in Table V (step 9).

Figure 6:
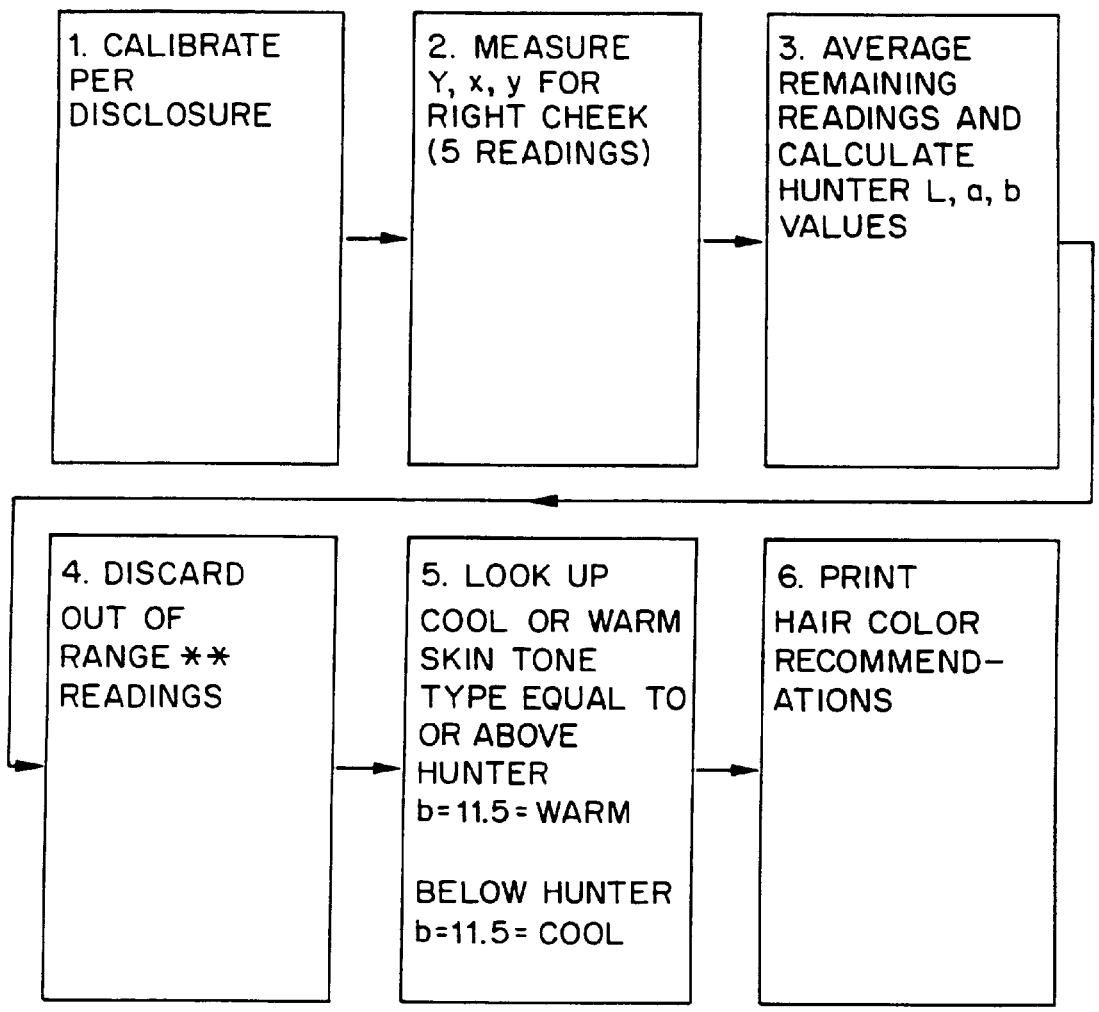
FIG. 6 is a schematic illustration in block diagram form illustrating the steps in the process of arriving at hair color treatment agents based upon a database of agents and individual skin color characteristics.

In FIG. 6 a method of using an indicator table to choose hair coloring agents for compatibility with skin coloration entails taking 5 measurements for the subjects right cheek and calculating Y, x and y (step 2), following calibration of the instrument (step 1). out of range readings are discarded prior to calculation of Hunter L, a and b based on the remaining three averaged Y, x and y readings (steps 3 and 4). Using the value of Hunter b at step 5 it is determined whether the skin tone type is less than 11.5 and consequently cool or equal to or higher than 11.5 and therefor warm. Using this cool or warm designation Table VII, set forth below is consulted to arrive at hair color recommendations (step 6).

TABLE VII

CALCULATION OF PERCENTAGE OF GREY HAIR

For Color Categories in Table I having grey (e.g. 61–68):

The "L" value of the natural hair (Site #1) and the value of the "L" from another site. If the other site's "L" value is from 1 to 2 points higher than the "L" of the natural hair, the category is: 40% to 60% Grey Hair.
If the other site's "L" value is above 2 points higher than the "L" of the natural hair, the category is: 70% to 90% Grey Hair.
If the "L" value is under 1 point increase from the most natural site (Site #1), then the category is: Low percentage of Grey Hair.

For Color Categories containing grey, not listed in Table I:

LIGHT BROWN/DARKEST BLOND HAIR:

| | |
|---|---|
| If "L" = +4 to +10 and "a" = −10.00 to −.80 | hair is 40%–60% Grey |
| If "L" = +10 or higher and "a" = −10.00 to −.80 | hair is 70%–90% Grey |

DARK RED, MEDIUM RED OR MEDIUM LIGHT RED HAIR:

| | |
|---|---|
| If "L" = +6 to +11 and "a" = −10.00 to −.80 | hair is 40%–60% Grey |
| If "L" = +11 or higher and "a" = −10.00 to −.80 | hair is 70%–90% Grey |

LIGHT RED OR RED BLONDE HAIR:

| | |
|---|---|
| If "L" = +5 to +7 and "a" = −10.00 to −.80 | hair is 40%–60% Grey |
| If "L" = −7 or higher and "a" = −10.00 to −.80 | hair is 70%–90% Grey |

MEDIUM TO MEDIUM DARK BLONDE HAIR:

| | |
|---|---|
| If "L" = +2 to +4 | hair is 40%–60% Grey |
| If "L" = +4 or higher | hair is 70%–90% Grey |

LIGHT BLONDE HAIR:

| | |
|---|---|
| If "L" = −.25 or less and "a" = −1.50 to −2.00 | hair is 40%–60% Grey |
| If "L" = .25 or less and "a" = −2.00 to higher | hair is 70%–90% Grey |

Table VII is developed by assessment of Hunter b in the products listed to assess the warmness or coolness of those products and products are recommended that have the same proportion of yellow to blue as does the measured skin color.

In FIG. 1 the calorimeter 10 provides Y, x and y to the computer 15. The computer's memory 17 is divided into RAM and ROM.

Figure 1A:
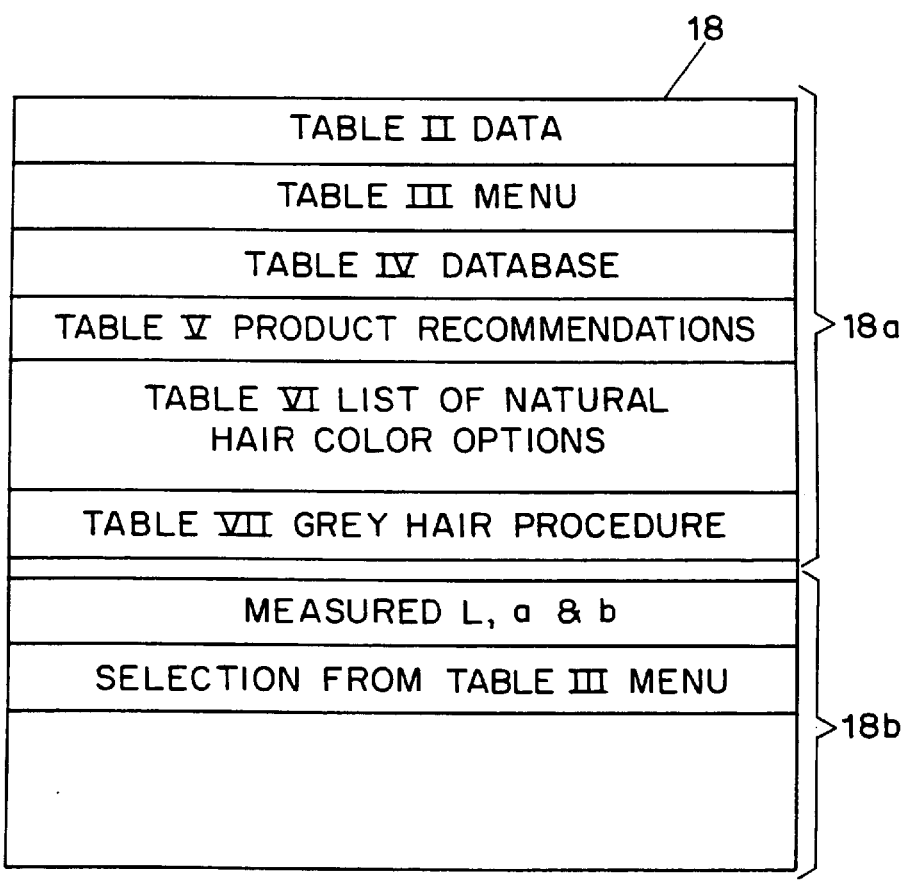
FIG. 1a is a diagrammatic illustration of exemplary memory content in an instrument like that of FIG. 1.

In the system of FIG. 1, following the routine of FIG. 2, the CPU or central processing unit of the computer calculates the Hunter values L, a and b and stores these at selected addresses of the data portion or RAM of memory 17. The data RAM (or nonprogram) portion 18 of the memory 17 is indicated in FIG. 1a. A relatively permanent section 18a of RAM 18 stores the data of Table II. A more often revised memory segment stores the results of the measurements performed with the instrument. Based on a relatively straightforward program retained in the permanent ROM memory, from the measurements taken at intervals, the CPU calculates new values of Hunter L, a and b. The CPU compares these to the Hunter L, a and b values in Table II and indicates the appropriate hair color category from Table II, for example on the display 20.

To perform the procedure according to FIG. 3, the RAM memory 18 contains as well the information of the menu of options in Table II. These are called up and displayed at display 20 and, using an input device such as a keyboard 22 or a mouse, a selection is made. The selection is retained in the more temporary portion 18b of the RAM 18.

The CPU consults the Table IV database, in the more permanent RAM section 18a and pulls up the appropriate manufacturer's product identifications in Table V, for the choice of menu items and the hair color category. These are displayed on the display 20.

To accomplish the procedure of FIG. 4 the computer 15's RAM 18 retains the Table II information which includes the greying hair categories 61 to 68 and the Table VII, information giving the manner of arriving at percentage of grey hair. The CPU inquires of the user via the display or measurement and is given the natural hair color via the input. The CPU uses the Hunter L, a and b values and Table II to determine Color Category or if Table II does not yield a category the Table VII information is employed with Hunter L to arrive at a Category using Table VII. The category is displayed.

To perform the procedures of FIG. 5 the CPU determines the category-percentage of grey hair as above, from either Table II or Table VII. The menu of selections, Table III is displayed and a choice is indicated. Using the choice and the category identified the Table IV database is used to indicate a group or "file" of manufacturer's products in Table V, which are then displayed on the display 20.

For the choice of hair coloring agent based on skin color the CPU determines if Hunter b is above or below 11.5.

While particular preferred embodiments of the invention have been described and illustrated, it will be apparent to those skilled in the art that revisions can be made without departure from the spirit and scope of the invention as defined in the appended claims.

I/we claim:

1. A process for analyzing the hair color of a subject, said process comprising the steps of:

(a) measuring with a measuring instrument a value of a first color factor in the coloration of said subject's hair, said first color factor being dependent on lightness of the coloration of said subject s hair;

(b) measuring with a measuring instrument a value of at least one further color factor in the coloration of said subject's hair, said farther color value being dependent on the relative content of opponent colors in the coloration of said subject's hair;

(c) wherein steps (a and (b) comprise arriving at values of said first color factor and said at least one further color factor that correlate to preestablished ranges of values of said color factors and that further correlate to measures of preestablished ranges of hair coloration; and (d) comparing the measured values of said first color factor and said at least one further color factor with said preestablished ranges of values of said color factors, to determine where within said ranges the measured values of said color factors lie.

2. The process according to claim 1, wherein at least one of steps (a) and (b) comprises arriving at the value of said first color factor or said at least one further color factor that correlates to a measure of preestablished ranges of hair coloration in subjects having hair colorations of substantially varying degrees of lightness or darkness.

3. The process according to claim 1 or 2, wherein at least one of steps (a) and (b) comprises arriving at the value of said first color factor or said at least one further color factor that correlates to a measure of preestablished ranges of hair coloration having established laboratory utility.

4. The process according to claim 1, wherein step (b) includes measuring the value of a color factor that is dependent on the relative content of red and green in the coloration of said subject's hair.

5. The process according to claim 1, wherein step (b) includes measuring the value of a color factor that is dependent on the relative content of blue and yellow in the coloration of said subject's hair.

6. The process according to claim 2, wherein step (b) comprises measuring with a measuring instrument the value of a color factor that is dependent on the relative content of blue and yellow in the coloration of said subject's hair.

7. The process according to claim 2, wherein step (b) comprises measuring with a measuring instrument the value of a color factor that is dependent on the relative content of red and green in the coloration of said subject's hair.

8. The process according to claim 3, wherein step (b) comprises measuring with a measuring instrument the value of a color factor that is dependent on the relative content of red and green in the coloration of said subject's hair.

9. The process according to claim 3, wherein step (b) comprises measuring with a measuring instrument the value of a color factor that is dependent on the relative content of red and green in the coloration of said subject's hair.

10. The process according to 1 or 2, wherein the color factors are selected from at least two of a color factor which is substantially that of color factor Hunter L, a color factor which is substantially that of color factor Hunter b and a color factor which is substantially that of color factor Hunter a.

11. The process according to claim 3, wherein the color factors are selected from at least two of a color factor which is substantially that of color factor Hunter L, a color factor which is substantially that of color factor Hunter b and a color factor which is substantially that of color factor Hunter a.

12. The process according to claim 11, wherein at least one of steps (a) and (b) comprises measuring the value of said color factor at different locations of the hair of said subject.

13. The process according to claim 1, wherein at least one of steps (a) and (b) comprises making a set of multiple measurements of the value of said color factor and averaging each set of multiple measurements.

14. The process according to any one of claims 1, or 2, wherein each of steps (a) and (b) for measuring with a measuring instrument the value of said color factor comprises measuring the value of said color factor at different locations of the hair of said subject.

15. The process according to any one of claims 1 or 2, wherein each of steps (a) and (b) for measuring with a measuring instrument the value of said color factor comprises making a set of multiple measurements of the value of said color factor and averaging each set of multiple measurements.

16. The process according to claim 3, wherein each of steps (a) and (b) for measuring with a measuring instrument the value of said color factor comprises measuring the value of said color factor at different locations of the hair of said subject.

17. The process according to claim 3, wherein each of steps (a) and (b) for measuring with a measuring instrument the value of said color factor comprises making a set of multiple measurements of the value of said color factor and averaging each set of multiple measurements.

* * * * *

UNITED STATES PATENT AND TRADEMARK OFFICE
CERTIFICATE OF CORRECTION

PATENT NO. : 6,067,504

DATED : May 23, 2000

INVENTOR(S) : Macfarlane et al.

Col. 18, Table IV: At 55, bMin, "1.75" should read -- 3.75 --;

Signed and Sealed this

Twelfth Day of December, 2000

Attest:

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 6,067,504
DATED : May 23, 2000
INVENTOR(S) : Macfarlane et al.

It is certified that error appears in the above-identified patent and that said Letters Patent is hereby corrected as shown below:

[63] Related U.S. Application Data: "Continuation-in-part of application No. 5,671,735, which is a continuation-in-part of application No. 08/021,657, Feb. 22, 1993, Pat. No. 5,313,267, which is a continuation of application No. 07/204,938, Jun. 6, 1998, abandoned, and application No. 06/904,369, Sep. 8, 1986, abandoned, and a continuation-in part of application No. 06/833,661, Feb. 21, 1986, abandoned, which is a continuation of application No. 06/514,618, Jul. 18, 1993, abandoned."

should read

-- This is a continuation-in-part of U.S. patent application Serial No. 08/239,733, filed May 9, 1994, and now patent No. 5,671,735. No right of priority is claimed based upon any application filed earlier than May 9, 1994. --

[56] References Cited, OTHER PUBLICATIONS: Insert -- DIALOG World Patent Index database abstract for Japanese patent application No. 257326, published Dec. 19, 1985 --

Col. 28, line 48: "subject s" should read -- subject's -- ;
Col. 28, line 52: "farther" should read -- further -- ;
Col. 28, line 55: "(a and (b)" should read -- (a) and (b) -- ;
Col. 29, line 28: "red and green" should read -- blue and yellow -- ;
Col. 30, line 7: "claim 11," should read -- claim 1, -- ;
Col. 30, line 15: "1," should read -- 1 -- ;
Col. 2, line 16: "calorimeter" should read -- colorimeter -- ;
Col. 3, line 20: "calorimeters" should read -- colorimeters -- ;
Col. 3, line 39: "calorimeter" should read -- colorimeter -- ;

UNITED STATES PATENT AND TRADEMARK OFFICE
CERTIFICATE OF CORRECTION

PATENT NO. : 6,067,504
DATED : May 23, 2000
INVENTOR(S) : Macfarlane et al.

It is certified that error appears in the above-identified patent and that said Letters Patent is hereby corrected as shown below:

Col. 3, line 47: "calorimeter" should read -- colorimeter -- ;
Col. 3, line 63: "calorim-" should read -- colorim- -- ;
Col. 3, line 67: "calorimeter" should read -- colorimeter -- ;
Col. 4, line 65: "calorimeter" should read -- colorimeter -- ;
Col. 5, line 20: "calorimeter" should read -- colorimeter -- ; and "block 10" should read -- block 10 --;
Col. 5, line 32: "calorimeter" should read -- colorimeter -- ;
Col. 6, line 27: "colorimeter 10" should read -- colorimeter 10 -- ;
Col. 7, Table II: At 6. C, a Min, "10.00" should read -- -10.00 -- ;
Col. 7, Table II: At 7. C, a Min, "10.00" should read -- -10.00 -- ;
Col. 7, Table II: At 13. D, Brown (Auburn Tones) - Cool, b Min, "10.00" should read -- -10.00 -- ;
Col. 7, Table II: "23. F" should read -- 21. F -- ;
Col. 7, Table II: At 30. I, L Max, "16.00" should read -- 36.00 -- ;
Col. 7, Table II: At 31. I, L Max, "16.00" should read -- 36.00 -- ;
Col. 9, Table II: At 32. I, L Max, "16.00" should read -- 36.00 -- ;
Col. 9, Table II: "38. F" should read -- 38. K -- ;
Col. 11, Table II: At 62. S, a Min, "-10.00" should read -- 10.00 -- ;
Col. 11, line 50: "3 #steps" should read -- 3, steps -- ;
Col. 13, Table IV: At 2, L Min, "34.00" should read -- 14.00 -- ;
Col. 13, Table IV: At 5, Clairol: "#3" should read -- #2 --; and L'Oreal: "M4" should read -- M3 -- ;
Col. 17, Table IV: "59" (first occurrence) should read -- 58 -- ;
Col. 17, Table IV: At 66, L'Oreal: "M7/M8" should read -- M9 -- ;
Col. 17, Table IV: At 67, L'Oreal: "M7/M8" should read -- M9 -- ;
Col. 19, line 20: "appendix" should read -- table -- ;
Col. 19, line 33: "In Table" should read -- In the Table -- ;

UNITED STATES PATENT AND TRADEMARK OFFICE
CERTIFICATE OF CORRECTION

PATENT NO. : 6,067,504
DATED : May 23, 2000
INVENTOR(S) : Macfarlane et al.

It is certified that error appears in the above-identified patent and that said Letters Patent is hereby corrected as shown below:

Col. 19, line 45: "turers" should read -- turer's -- ;
Col. 26, line 42: "Table VII, set forth below" should read -- (Table VII, set forth below) -- ;
Col. 27, line 1: "subjects" should read -- subject's -- ;
Col. 27, line 3: "out" should read -- Out -- ;
Col. 27, line 8: "therefor" should read -- therefore -- ;
Col. 27, line 9: "designation" should read -- designation, -- ;
Col. 27, line 56: "calorimeter" should read -- colorimeter -- ;
Col. 28, line 8: "Table II." should read -- Table III. -- ;
Col. 28, line 19: "Table VII," should read -- Table VII -- ;
Col. 28, line 26: "Category" should read -- category -- .

Signed and Sealed this

Eighth Day of May, 2001

NICHOLAS P. GODICI

Attest:

Attesting Officer

Acting Director of the United States Patent and Trademark Office